United States Patent
Reisner et al.

(10) Patent No.: US 11,497,776 B2
(45) Date of Patent: *Nov. 15, 2022

(54) COMBINATION THERAPY FOR A STABLE AND LONG TERM ENGRAFTMENT

(71) Applicant: Yeda Research and Development Co. Ltd., Rehovot (IL)

(72) Inventors: Yair Reisner, Houston, TX (US); Esther Bachar-Lustig, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 223 days.

This patent is subject to a terminal disclaimer.

(21) Appl. No.: 16/508,325

(22) Filed: Jul. 11, 2019

(65) Prior Publication Data
US 2019/0328793 A1 Oct. 31, 2019

Related U.S. Application Data

(63) Continuation of application No. 14/367,917, filed as application No. PCT/IL2012/050542 on Dec. 20, 2012, now Pat. No. 10,369,172.

(60) Provisional application No. 61/578,917, filed on Dec. 22, 2011.

(51) Int. Cl.
| | |
|---|---|
| *A61K 35/28* | (2015.01) |
| *A61K 35/17* | (2015.01) |
| *A61K 35/22* | (2015.01) |
| *A61K 35/38* | (2015.01) |
| *A61K 35/39* | (2015.01) |
| *A61K 35/407* | (2015.01) |
| *A61K 35/42* | (2015.01) |
| *A61K 31/675* | (2006.01) |
| *A61K 35/34* | (2015.01) |
| *A61K 35/36* | (2015.01) |
| *C12N 5/00* | (2006.01) |
| *A61K 31/198* | (2006.01) |
| *A61K 31/255* | (2006.01) |
| *A61K 31/7076* | (2006.01) |
| *A61P 37/06* | (2006.01) |
| *A61P 37/02* | (2006.01) |
| *A61K 31/661* | (2006.01) |
| *A61K 39/395* | (2006.01) |
| *A61K 39/00* | (2006.01) |
| *A61K 35/12* | (2015.01) |

(52) U.S. Cl.
CPC ............ *A61K 35/28* (2013.01); *A61K 31/198* (2013.01); *A61K 31/255* (2013.01); *A61K 31/661* (2013.01); *A61K 31/675* (2013.01); *A61K 31/7076* (2013.01); *A61K 35/22* (2013.01); *A61K 35/34* (2013.01); *A61K 35/36* (2013.01); *A61K 35/38* (2013.01); *A61K 35/39* (2013.01); *A61K 35/407* (2013.01); *A61K 35/42* (2013.01); *A61K 39/3955* (2013.01); *A61P 37/02* (2018.01); *A61P 37/06* (2018.01); *C12N 5/0087* (2013.01); *A61K 2035/124* (2013.01); *A61K 2039/507* (2013.01); *A61K 2039/515* (2013.01); *C12N 2501/06* (2013.01)

(58) Field of Classification Search
CPC ... A61K 35/28; A61K 2035/124; A61P 37/06; C12N 5/0087
See application file for complete search history.

(56) References Cited

U.S. PATENT DOCUMENTS

| | | | |
|---|---|---|---|
| 5,514,364 A | 5/1996 | Ildstad | |
| 5,635,156 A | 6/1997 | Ildstad | |
| 5,806,529 A | 9/1998 | Reisner et al. | |
| 5,876,692 A | 3/1999 | Ildstad | |
| 5,928,639 A | 7/1999 | Slavin | |
| 6,039,684 A | 3/2000 | Ildstad et al. | |
| 6,217,867 B1 | 4/2001 | Ildstad | |
| 6,491,917 B1 | 12/2002 | Thomas et al. | |
| 6,544,787 B1 | 4/2003 | Slavin | |
| 10,369,172 B2 * | 8/2019 | Reisner | .......... A61K 35/28 |
| 10,434,121 B2 * | 10/2019 | Reisner | .......... A61K 35/36 |
| 2001/0009663 A1 | 7/2001 | Ildstad | |

(Continued)

FOREIGN PATENT DOCUMENTS

| | | |
|---|---|---|
| AU | 2003204277 | 6/2003 |
| WO | WO 99/25367 | 5/1999 |

(Continued)

OTHER PUBLICATIONS

Luznik et al., High-dose cyclophosphamide as single-agent, short-courseprophylaxis of graft-versus-host disease, Blood, 115(16): 3224-3230. (Year: 2010).*

(Continued)

*Primary Examiner* — Hong Sang

(57) ABSTRACT

A method of treating a subject in need of a non-syngeneic cell or tissue graft is disclosed. The method comprising: (a) transplanting into a subject a dose of T cell depleted immature hematopoietic cells, wherein the T cell depleted immature hematopoietic cells comprise less than $5 \times 10^5$ CD3+ T cells per kilogram body weight of the subject, and wherein the dose comprises at least about $5 \times 10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

22 Claims, 7 Drawing Sheets

(7 of 7 Drawing Sheet(s) Filed in Color)

(56) References Cited

U.S. PATENT DOCUMENTS

| | | | |
|---|---|---|---|
| 2003/0017152 | A1 | 1/2003 | Ildstad |
| 2003/0165475 | A1* | 9/2003 | Ildstad ............... A61K 41/00 |
| | | | 424/93.7 |
| 2004/0005300 | A1 | 1/2004 | Ildstad |
| 2004/0023377 | A1 | 2/2004 | Assenmacher et al. |
| 2004/0185043 | A1 | 9/2004 | Ildstad |
| 2005/0118142 | A1 | 6/2005 | Ildstad |
| 2006/0140912 | A9 | 6/2006 | Ildstad |
| 2007/0098693 | A1 | 5/2007 | Ildstad |
| 2007/0141027 | A1 | 6/2007 | Ildstad |
| 2011/0110909 | A1 | 5/2011 | Ildstad et al. |
| 2014/0363437 | A1 | 12/2014 | Reisner et al. |
| 2014/0369974 | A1 | 12/2014 | Reisner et al. |
| 2019/0358269 | A1 | 11/2019 | Reisner et al. |

FOREIGN PATENT DOCUMENTS

| | | | |
|---|---|---|---|
| WO | WO 02/40640 | | 5/2002 |
| WO | WO-2009094456 A2 * | 7/2009 | ........... A61K 31/675 |
| WO | WO 2013/093919 | | 6/2013 |
| WO | WO 2013/093920 | | 6/2013 |

OTHER PUBLICATIONS

Luznik et al., High-dose, post-transplantation cyclophosphamide to promote graft-host tolerance after allogeneic hematopoietic stem cell transplantation, Immunol Res., 47(1-3): 65-77. (Year: 2010).*
Luznik et al., High-dose cyclophosphamide for GVHD prevention, Curr Opin Hematol., 17(6):493-9. (Year: 2010).*
Written Opinion dated Jun. 4, 2020 From the Intellectual Property Office of Singapore Re. Application No. 10201801905W. (7 Pages).
Advisory Action Before the Filing of An Appeal Brief dated Feb. 1, 2018 From the US Patent and Trademark Office Re. U.S. Appl. No. 14/367,917. (3 pages).
Applicant-Initiated Interview Summary Dated Mar. 4, 2019 From the US Patent and Trademark Office Re. U.S. Appl. No. 14/367,917. (3 pages).
Applicant-Initiated Interview Summary Dated Dec. 7, 2017 From the US Patent and Trademark Office Re. U.S. Appl. No. 14/367,923. (3 pages).
Communication Pursuant to Article 94(3) EPC dated Jan. 4, 2019 From the European Patent Office Re. Application No. 12859036.1. (4 Pages).
Communication Pursuant to Article 94(3) EPC dated Jul. 12, 2017 From the European Patent Office Re. Application No. 12861023.5. (7 Pages).
Communication Pursuant to Article 94(3) EPC dated May 15, 2018 From the European Patent Office Re. Application No. 12859036.1. (5 Pages).
Decision of Rejection dated Oct. 2, 2018 From the Japan Patent Office Re. Application No. 2018-007779 and Its Machine Translation Into English. (3 Pages).
Examination Report dated May 5, 2016 From the Intellectual Property Office of Singapore Issued by the Austrian Patent Office Re. Application No. 11201403456U.
Examination Report dated Jun. 6, 2018 From the Instituto Mexicano de la Propiedad Industrial, IMPI, Direccion Divisional de Patentes Re. Application No. MX/a/2014/007647 and Its Translation Into English. (10 Pages).
Examination Report dated Jun. 16, 2017 From the Australian Government, IP Australia Re. Application No. 2016259415. (4 Pages).
Examination Report dated Oct. 16, 2018 From the Instituto Mexicano de la Propiedad Industrial, Direccion Divisional de Patentes, IMPI Re. Application No. MX/a/2014/007648 and Its Translation Into English. (10 Pages).
Examination Report dated Feb. 22, 2019 From the Instituto Mexicano de la Propiedad Industrial, IMPI, Direccion Divisional de Patentes Re. Application No. MX/a/2014/007647. (5 Pages).
Examination Report dated May 22, 2019 From the Institute Mexicano de la Propiedad Industrial, Direccion Divisional de Patentes, IMPI Re. Application No. MX/a/2014/007648 and Its Translation Into English. (14 Pages).
Examination Report dated Feb. 28, 2018 From the Instituto Mexicano de la Propiedad Industrial, Direccion Divisional de Patentes, IMPI Re. Application No. MX/a/2014/007648 and Its Translation Into English. (10 Pages).
Examination Report dated Oct. 31, 2017 From the Instituto Mexicano de la Propiedad Industrial, IMPI, Direccion Divisional de Patentes Re. Application No. MX/a/2014/007647 and Its Translation Into English. (10 Pages).
Examination Report Under Sections 12 & 13 of the Patents Act, 1970 and the Patents Rules, 2003 dated Jan. 11, 2019 From the Government of India, Intellectual Property India, Patents, Designs, Trade Marks, Geographical Indications Re. Application No. 1468/MUMNP/2014. (6 Pages).
Examination Report Under Sections 12 & 13 of the Patents Act, 1970 and the Patents Rules, 2003 dated Jan. 28, 2019 From the Government of India, Intellectual Property India, Patents, Designs, Trade Marks, Geographical Indications Re. Application No. 1467/MUMNP/2014. (20 Pages).
Grounds of Reasons for Rejection dated Apr. 1, 2019 From the Korean Intellectual Property Office Re. Application No. 10-2014-7020449. (7 Pages).
International Preliminary Report on Patentability dated Jul. 3, 2014 From the International Bureau of WIPO Re. Application No. PCT/IL2012/050541.
International Preliminary Report on Patentability dated Oct. 23, 2014 From the International Bureau of WIPO Re. Application No. PCT/IL2012/050542.
International Search Report and the Written Opinion dated Jun. 10, 2013 From the International Searching Authority Re. Application No. PCT/IL2012/050541.
International Search Report and the Written Opinion dated May 13, 2013 From the International Searching Authority Re. Application No. PCT/IL2012/050542.
Notice of Acceptance dated Sep. 28, 2017 From the Australian Government, IP Australia Re. Application No. 2012355990. (9 Pages).
Notice of Reason for Rejection dated Sep. 1, 2016 From the Japan Patent Office Re. Application No. 2014-548336 and Its Translation Into Enghsh.
Notice of Reason for Rejection dated Mar. 14, 2017 From the Japan Patent Office Re. Application No. 2014-548336 and Its Translation Into Enghsh. (9 Pages).
Notification of Decision of Rejection dated Apr. 11, 2018 From the State Intellectual Property Office of the People's Republic of China Re. Application No. 201280068917.4 and Its Translation Into English. (6 Pages).
Notification of Decision of Rejection dated Sep. 27, 2018 From the State Intellectual Property Office of the People's Republic of China Re. Application No. 201280068202.9. (5 Pages).
Notification of Office Action and Search Report dated Jun. 15, 2017 From the State Intellectual Property Office of the People's Republic of China Re. Application No. 201280068202.9. (8 Pages).
Notification of Office Action and Search Report dated Jan. 28, 2016 From the State Intellectual Property Office of the People's Republic of China Re. Application No. 201280068202.9.
Notification of Office Action and Search Report dated Jun. 30, 2015 From the State Intellectual Property Office of the People's Republic of China Re. Application No. 201280068917.4 and Its Translation of Office Action Into English.
Notification of Office Action dated Oct. 14, 2016 From the State Intellectual Property Office of the People's Republic of China Re. Application No. 201280068202.9.
Notification of Reexamination dated Apr. 15, 2019 From the State Intellectual Property Office of the People's Republic of China Re. Application No. 201280068917.4 and Its Summary in English. (7 Pages).
Notification of Refusal and Examination Report dated Mar. 22, 2016 From the Intellectual Property Office of Singapore Re. Application No. 11201403459X.

(56) References Cited

OTHER PUBLICATIONS

Office Action and Search Report dated May 5, 2016 From the State Intellectual Property Office of the People's Republic of China Re. Application No. 201280068917.4.
Office Action dated Mar. 14, 2017 From the Israel Patent Office Re. Application No. 233302 and Its Translation Into English. (6 Pages).
Office Action dated Mar. 15, 2018 From the Israel Patent Office Re. Application No. 233303 and Its Translation Into English. (6 Pages).
Official Action dated Mar. 7, 2017 From the US Patent and Trademark Office Re. U.S. Appl. No. 14/367,917. (47 pages).
Official Action dated Aug. 15, 2017 From the US Patent and Trademark Office Re. U.S. Appl. No. 14/367,923. (26 pages).
Official Action dated Sep. 19, 2018 From the US Patent and Trademark Office Re. U.S. Appl. No. 14/367,917. (27 pages).
Official Action dated Feb. 23, 2017 From the US Patent and Trademark Office Re. U.S. Appl. No. 14/367,923. (63 pages).
Official Action dated Oct. 26, 2017 From the US Patent and Trademark Office Re. U.S. Appl. No. 14/367,917. (34 pages).
Official Action dated Oct. 26, 2018 From the US Patent and Trademark Office Re. U.S. Appl. No. 14/367,923. (28 pages).
Official Action dated Mar. 27, 2018 From the US Patent and Trademark Office Re. U.S. Appl. No. 14/367,917. (18 pages).
Official Action dated Mar. 27, 2018 From the US Patent and Trademark Office Re. U.S. Appl. No. 14/367,923. (22 pages).
Official Decision of Rejection dated Sep. 22, 2017 From the Japan Patent Office Re. Application No. 2014-548336 and Its Translation Into English. (5 Pages).
Patent Examination Report dated Nov. 19, 2015 From the Australian Government, IP Australia Re. Application No. 2012355989.
Patent Examination Report dated Oct. 21, 2016 From the Australian Government, IP Australia Re. Application No. 2012355989.
Patent Examination Report dated Oct. 21, 2016 From the Australian Government, IP Australia Re. Application No. 2012355990.
Request for Examination dated Sep. 28, 2016 From the ROSPATENT, Federal Government Institution, Federal Institute of Industrial Property of the Federal Service for Intellectual Property, Patents and Trademark of the Russian Federation Re. Application No. 2014128479 and Its Translation Into English. (8 Pages).
Request for Examination dated Sep. 28, 2016 From the ROSPATENT, Federal Government Institution, Federal Institute of Industrial Property of the Federal Service for Intellectual Property, Patents and Trademarks of the Russian Federation Re. Application No. 2014129632 and Its Translation Into English. (12 Pages).
Requisition by the Examiner dated Oct. 18, 2018 From the Innovation, Science and Economic Development Canada, Canadian Intellectual Property Office Re. Application No. 2,859,952. (5 Pages).
Requisition by the Examiner dated Oct. 18, 2018 From the Innovation, Science and Economic Development Canada, Canadian Intellectual Property Office Re. Application No. 2,859,953. (18 Pages).
Restriction Official Action dated Oct. 6, 2016 From the US Patent and Trademark Office Re. U.S. Appl. No. 14/367,917.
Restriction Official Action dated Oct. 6, 2016 From the US Patent and Trademark Office Re. U.S. Appl. No. 14/367,923.
Search Report and Written Opinion dated Mar. 8, 2019 From the Intellectual Property Office of Singapore Re. Application No. 10201801905W. (12 Pages).
Search Report and Written Opinion dated Jan. 9, 2015 From the Intellectual Property Office of Singapore Issued by the Austrian Patent Office Re. Application No. 11201403456U.
Search Report and Written Opinion dated Dec. 15, 2014 From the Intellectual Property Office of Singapore Re. Application No. 11201403459X.
Supplementary European Search Report and the European Search Opinion dated Jan. 12, 2016 From the European Patent Office Re. Application No. 12859036.1.
Supplementary European Search Report and the European Search Opinion dated Jul. 29, 2015 From the European Patent Office Re. Application No. 12861023.5.

Translation Dated Apr. 11, 2019 of Grounds of Reasons for Rejection dated Apr. 1, 2019 From the Korean Intellectual Property Office Re. Application No. 10-2014-7020449. (6 Pages).
Translation Dated Feb. 14, 2016 of Notification of Office Action dated Jan. 28, 2016 From the State Intellectual Property Office of the People's Republic of China Re. Application No. 201280068202.9.
Translation Dated Oct. 15, 2018 of Notification of Decision of Rejection dated Sep. 27, 2018 From the State Intellectual Property Office of the People's Republic of China Re. Application No. 201280068202.9. (8 Pages).
Translation Dated Mar. 27, 2019 of Examination Report dated Feb. 22, 2019 From the Institute Mexicano de la Propiedad Industrial, IMPI, Direccion Divisional de Patentes Re. Application No. MX/a/2014/007647. (2 Pages).
Translation of Notification of Office Action dated Oct. 14, 2016 From the State Intellectual Property Office of the People's Republic of China Re. Application No. 201280068202.9.
Translation of Notification of Office Action dated Jun. 15, 2017 From the State Intellectual Property Office of the People's Republic of China Re. Application No. 201280068202.9. (5 Pages).
Translation of Office Action dated May 5, 2016 From the State Intellectual Property Office of the People's Republic of China Re. Application No. 201280068917.4.
Written Opinion dated Aug. 12, 2015 From the Intellectual Property Office of Singapore Issued by the Austrian Patent Office Re. Application No. 11201403459X.
Written Opinion dated Aug. 18, 2015 From the Intellectual Property Office of Singapore issued by the Austrian Patent Office Re. Application No. 11201403456U.
Aversa et al. "Full Haplotype-Miismatched Hematopoietic Stem-Cell Transplantation: A Phase II Study in Patients With Acute Leukemia at High Risk of Relapse", Journal Of Clinical Oncology. 23(15): 3447-3454, May 20, 2005.
Aversa et al. "Treatment of High-Risk Acute Leukemia With T-Cell-Depleted Stem Cells Related Donors With One Fully Mismatched HLA Haplotype", The New England Journal of Medicine, 339(17): 1186-1193, Oct. 22, 1998.
Bachar-Lustig et al. "Megadose of T Cell-Depleted Bone Marrow Overcomes MHC Barriers in Sublethally Irradiated Mice", Nature Medicine, 1(12): 1268-1273, Dec. 1995.
Barfield et al. "A One-Step Large-Scale Method for T- and B-Cell Depletion of Mobilized PBSC for Allogeneic Transplantation", Cyotherapy, 6(1): 1-6, Jan. 2004. Abstract,.
Bethge et al. "Haploidentical Allogeneic Hematopoietic Cell Transplantation in Adults Using CD3/CD19 Depletion and Reduced Intensity Conditioning: An Update", Blood Cells, Molecules, and Diseases, 40(1): 13-19, Published Online Sep. 14, 2007.
Bomberger et al. "Lymphoid Reconstitution After Autologous PBSC Transplantation With FACS-Sorted CD34+ Hematopoietic Progenitors", Blood, XP002487975, 91(7): 2588-2600, Apr. 1, 1998. Abstract, p. 2589, 1-h Col. Para 2—p. 2590, 1-h Col., Para 1, p. 2595, 1-h Col., Para 1—p. 2599, 1-h Col., Para 1.
Brodsky et al. "Aplastic Anaemia", The Lancet, 365: 1647-1656, May 7, 2005.
De Pauw et al. "Isolation and Infusion of Donor CD34+ Bone Marrow Cells in Cadaver Kidney Transplantation", Nephrology Dialysis Transplantation, 13(1): 34-36, Jan. 1998. Abstract, p. 35, col. 2, Para 1, p. 34, col. 2, Para 2-3.
Dykes et al. "Rapid and Effective CD3 T-Cell Depletion With A Magnetic Cell Sorting Program to Produce Peripheral Blood Progenitor Cell Products for Haploidentical Transplantation in Children and Adults", Transfusion, 47(11): 2134-2142, Nov. 2007. Table 1, Abstract, p. 2135, col. 1, Para 4—col. 2, Para 2, p. 2136, col. 2, Para 2.
Fugier-Vivier et al. "Plasmacytoid Precursor Dendritic Cells Facilitate Allogeneic Hematopoietic Stem Cell Engraftment", The Journal of Experimental Medicine, 201(3): 373-383, Feb. 7, 2005.
Handgretinger et al. "The History and Future Prospective of Haplo-Identical Stem Cell Transplantation", Cytotherapy, XP055203084, 10(5): 443-451, Jan. 1, 2008 2008. Abstract, p. 444, r-h Col., Para 3—p. 445, r-h Col., Para 3.

(56) References Cited

OTHER PUBLICATIONS

Huang et al. "CD8[Alpha]+ Plasmacytoid Precursor DCs Induce Antigen-Specific Regulatory T Cells That Enhance HSC Engraftment In Vivo", Blood, 117(8): 2494-2505, Feb. 24, 2011.
Kaufman et al. "Phenotypic Characterization of A Novel Bone Marrow-Derived Cell That Facilitates Engraftment of Allogeneic Bone Marrow Stem Cells", Blood, 84(8): 2436-2446, Oct. 15, 1994.
Koh et al. "Haploidentical Haematopoietic Stem Cell Transplantation Using CD3 or CD3/CD19 Depletion and Conditioning with Fludarabine, Cyclophosphamide and Antithymocyte Globulin for Acquired Severe Aplastic Anaemia", British Journal of Haematology, XP055202937, 157(1): 139-142, Apr. 2012. p. 139-141.
Leighton Grimes et al. "Graft Facilitating Cells Are Derived From Hematopoietic Stem Cells and Functionally Require CD3, But Are Distinct From T Lymphocytes", Experimental Hematology, 32(10): 946-954, Oct. 2004.
Leventhal et al. "Chimerism and Tolerance Without GVHD or Engraftment Syndrome in HLA-Mismatched Combined Kidney and Hematopoietic Stem Cell Transplantation", Science Translational Medicine, 4(124ra28): 1-10, Mar. 7, 2012.
Leventhal et al. "Chimerism, Lymphocyte Recovery, and the Absence of Graft-Versus-Host Disease in Recipients of Mismatched Unrelated Combined Kidney and HSC Transplants for Tolerance Induction", Blood, ASH Annual Meeting Abstracts, 118: # 1969, 2011.
Leventhal et al. "Novel Regulatory Therapies for Prevention of Graft-Versus-Host Disease", BMC Medicine, 10(48): 1-8, Published Online May 15, 2012.
Luznik et al. "HLA-Haploidentical Bone Marrow Transplantation for Hematologic Malignancies Using Nonmyeloablative Conditioning and High-Dose, Posttransplantation Cyclophosphamide", Biology of Blood and Marrow Transplantation, 14(6): 641-650, Jun. 2008. Fig.1, Abstract, p. 642, col. 1, Para 3, p. 643, col. 1, Para 2.
Munchel et al. "Nonmyeloablative, HLA-Haploidentical Bone Marrow Transplantation With High Dose. Post-Transplantation Cyclophosphamide", Pediatric Reports, 2(S2/e15): 43-47, Jun. 2011.
Nakai et al. "Value of Chemotherapy Before Allogeneic Hematopoietic Stem Cell Transplantation From An HLA-Identical Sibling Donor for Myelodysplastic Syndrome", Leukemia, 19(3): 396-401, Published Online Jan. 13, 2005.
O'Donnell et al. "Nonmyeloablative Bone Marrow Transplantation From Partially HLA-Mismatched Related Donors Using Posttransplantation Cyclophosphamide", Biology of Blood and Marrow Transplantation, 8(7): 377-386, Jul. 2002.
Ogawa et al. "Unmanipulated HLA 2-3 Antigen-Mismatched (Haploidentical) Stem Cell Transplantation Using Nonmyeloablative Conditioning", Biology of Blood and Marrow Transplantation, 12(10): 1073-1084, Oct. 2006.
Ogura et al. "Phase I/II Trial of Cure-Oriented High-Dose Chemoradiotherapy With Transplantation of CD34+ Peripheral Blood Stem Cells Purified by the Immunomagnetic Bead Method for Refractory Hematological Malignancies", Cancer Chemotherapy and Pharmacology, 40(Suppl.): S51-S57, Jun. 1997.
Owens et al. "The Effect of Cytotoxic Drugs on Graft-Versus-Host Disease in Mice", Transplantation, 11(4): 378-382, Apr. 1971.
Passweg et al. "Increased Stem Cell Dose, as Obtained Using Currently Available Technology, May Not Be Sufficient for Engraftment of Haploidentical Stem Cell Transplants", Bone Marrow Transplantation, XP055203062, 26(10): 1033-1036, Nov. 2000. Abstract, p. 1033, r-h Col., Para 2—p. 1034, 1-h Col., Para 1, p. 1035, 1-h Col., Para 2—r-h Col., Para 4.
Prigozhina et al. "Prevention of Acute Graft-Vs-Host Disease by A Single Low-Dose Cyclophosphamide Injection Following Allogeneic Bone Marrow Transplantation", Experimental Hematology, 36(12): 1750-1759, Sep. 21, 2008.
Reisner et al. "Bone Marrow Transplantation Across HLA Barriers by Increasing the Number of Transplanted Cells", Immunology Today, 16(9): 437-440, Sep. 1995.
Richel et al. "Highly Purified CD34+ Cells Isolated Using Magnetically Activated Cell Selection Provide Rapid Engraftment Following High-Dose Chemotherapy in Breast Cancer Patients", Bone Marrow Transplantation, 25(3): 243-249, Feb. 2000. p. 243, col. 2, Para 2, p. 244, col. 2, Para 4—p. 245, col. 1, Para 1.
Seggewiss et al. "Immune Reconstitution After Allogeneic Transplantation and Expanding Options for Immunomodulation: An Update", Blood, 115(19): 3861-3868, Published Online Mar. 9, 2010.
Sharabi et al. "Mixed Chimerism and Permanent Specific Transplantation Tolerance Induced by A Nonlethal Preparative Regimen", The Journal of Experimental Medicine, 169(2): 493-502, Feb. 1989.
Smetak et al. "Clinical-Scale Single-Step CD4 + and CD8+ Cell Depletion for Donor Innate Lymphocyte Infusion (DILI)", Bone Marrow Transplantation, 41(7): 643-650, Apr. 2008. Abstract, p. 644, col. 1, Para 4, p. 648, col. 2, Para 3.
Examination Report dated Dec. 7, 2020 From the Servico Publico Federal, Ministerio da Economia, Instituto Nacional da Propriedade Industrial do Brasil RE Application No. BR112014015959 9 and Its Summary Into English. (7 Pages).
Official Action dated Jul. 23, 2021 from the US Patent and Trademark Office Re. U.S. Appl. No. 16/538,954. (44 pages).
Final Official Action dated Jan. 25, 2022 from US Patent and Trademark Office Re. U.S. Appl. No. 16/538,954. (16 pages).

* cited by examiner

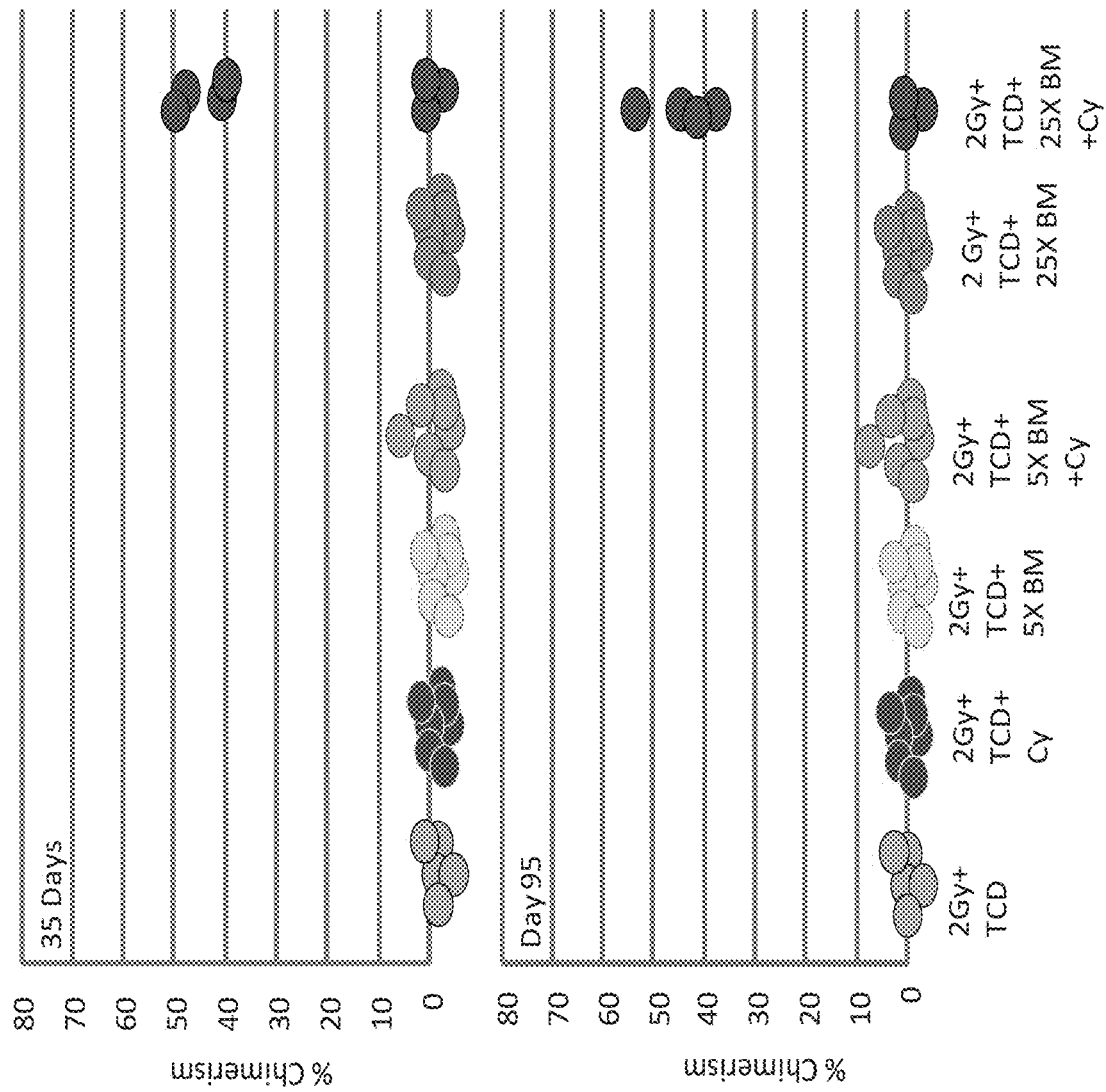

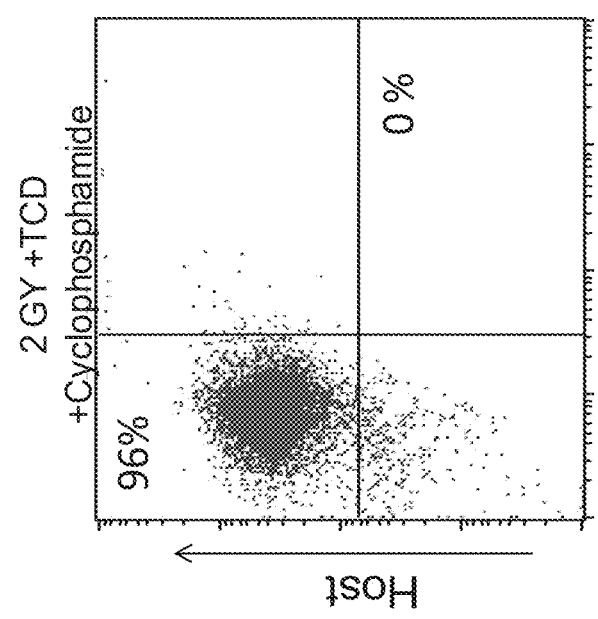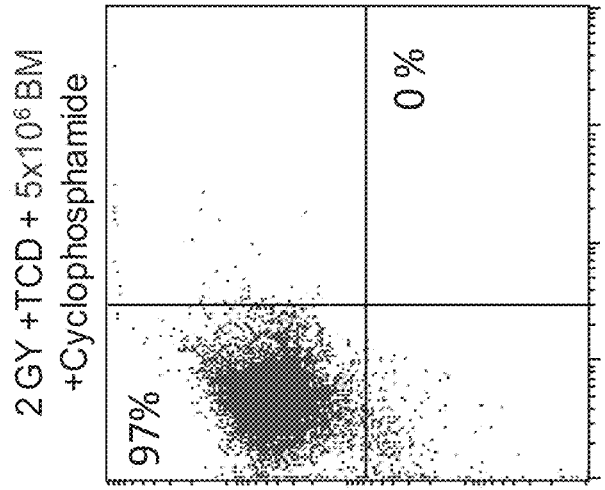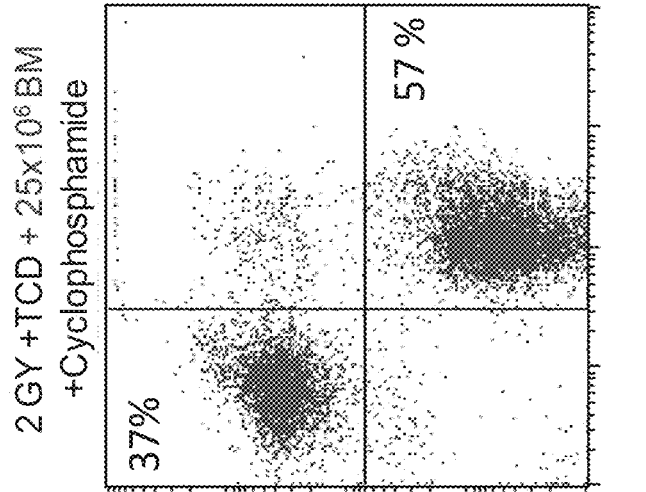

COMBINATION THERAPY FOR A STABLE AND LONG TERM ENGRAFTMENT

RELATED APPLICATIONS

This application is a continuation of U.S. patent application Ser. No. 14/367,917 filed on Jun. 22, 2014, which is a National Phase of PCT Patent Application No. PCT/IL2012/050542 having International Filing Date of Dec. 20, 2012, which claims the benefit of priority under 35 USC § 119(e) of U.S. Provisional Patent Application No. 61/578,917 filed on Dec. 22, 2011. The contents of the above applications are all incorporated by reference as if fully set forth herein in their entirety.

FIELD AND BACKGROUND OF THE INVENTION

The present invention, in some embodiments thereof, relates to a combination therapy for attaining a stable and long term cell or tissue transplantation.

The use of full-haplotype mismatched haploidentical donors as an alternative source for hematopoietic stem cell transplantation (HSCT) is highly attractive since virtually all patients have a readily available haploidentical family member that can serve as an HSCT donor. Early attempts to avoid fatal graft versus host disease (GVHD) risk and to apply haploidentical rigorously T cell depleted bone marrow transplantation (TDBMT) in leukemia patients revealed that the absence of donor T cells within the graft leads to a high rate of graft rejection, mediated by residual radiotherapy and chemotherapy resistant host-derived T cells (HTC). To overcome this obstacle, a 'mega dose' of TDBM cells was contemplated which can overcome this HTC mediated immune barrier and be engrafted successfully even when using fully mismatched murine strain combinations [Bachar-Lustig E et al., *Nat Med*. (1995) 1:1268-1273]. Subsequently, it was demonstrated that in humans, as in rodents, $CD34^+$ hematopoietic stem cell dose escalation may be used to overcome genetic barriers, enabling satisfactory survival rates following purified haploidentical HSCT [Reisner Y and Martelli M F. *Immunol Today*. (1995) 16:437-440 and U.S. Pat. No. 5,806,529].

While the use of a purified 'mega dose' of $CD34^+$ HSCT has enabled haploidentical transplantation in leukemia patients, one major drawback, common to all T cell depleted transplants, is the slow recovery rate of the recipient's immune system. This is attributed to extensive immune ablating conditioning protocols prior to transplantation, the low numbers of donor T cells infused within the graft and to the decreased thymic function of adult recipients. Thus, in adult recipients of a haploidentical $CD34^+$ stem cell graft, a significant rate of transplant related mortality (TRM) is caused by opportunistic infections.

Several approaches are being developed to address this challenge. This includes novel modalities to improve thymic function, post-transplant adoptive transfer of anti-viral specific T cells, transfer of partially polyclonal host-non-reactive allo-depleted T cells or transfer of fully polyclonal T cells transfected with inducible suicide genes. An alternative and additional approach to preserve host immunity is the use of reduced intensity conditioning (RIC). This non-myeloablative approach spares a substantial level of host immune cells and thus may reduce TRM by both improving post-transplant immune reconstitution and reducing the toxicity associated with the conditioning agents. Haploidentical transplantation under RIC is even more intricate due to the substantial immunological barrier presented by the surviving host T cells. Recent attempts to overcome this barrier, largely made use of non-T cell depleted grafts, which enable a high rate of engraftment, but in the expanse of increased rates of GVHD. Another approach for applying haploidentical transplantation under RIC uses CD3/CD19 depleted grafts, which not only contain $CD34^+$ stem cells but also CD34 negative progenitors, NK, graft facilitating cells and dendritic cells, however, this too is at the expanse of increased rates of GVHD and TRM.

In the 1970's George Santos demonstrated in rodents that a short course of high-dose cyclophosphamide (CY) soon after bone marrow transplant (BMT) targeted activated donor or host alloreactive T cells [Owens A H Jr and G W. S. Transplantation. (1971) 11:378-382]. Cyclophosphamide was observed to be non-toxic to hematopoietic stem cells because of their high expression of the detoxifying enzyme aldehyde dehydrogenase, and Slavin et al. further demonstrated that administration of high dose cyclophosphamide can reduce GVHD and graft rejection in mice, without adverse effects on stem cell engraftment [Brodsky R A and RJ. *J. Lancet*. (2005) 365:1647-1656]. Clinical trials by the John Hopkins and Fred Hutchinson Cancer Research Center groups, evaluated a non-myeloablative protocol of cyclophosphamide, fludarabine and 2Gy TBI, and post-transplant GVHD prophylaxis with cyclophosphamide (50 mg/kg days +3 and +4), MMF (days +5 to +35) and tacrolimus (days +5 to +180) [Luznik L et al., *Biology of blood and marrow transplantation: journal of the American Society for Blood and Marrow Transplantation*. (2008) 14:641]. According evident from their teachings, this protocol resulted in a high relapse rate, which was probably due to poor disease debulking by the non-myeloablative conditioning and to lack of GVHD related graft versus leukemia (GVL) effect [Munchel A et al., *Pediatric Reports* (2011) 3:43-47].

Additional approaches for achieving stable engraftment of allogeneic hematopoietic stem cells have been attempted, some are described in U.S. Patent Application No. 20110110909, U.S. Patent Application No. 20050118142, U.S. Patent Application No. 20070098693, U.S. Pat. Nos. 5,876,692, 5,514,364, 6,217,867, 5,635,156, U.S. Patent Application No. 20060140912, U.S. Patent Application No. 20040005300, U.S. Patent Application No. 20070141027, U.S. Patent Application No. 20030017152, U.S. Patent Application No. 20030165475 and U.S. Patent Application No. 20010009663.

SUMMARY OF THE INVENTION

According to an aspect of some embodiments of the present invention there is provided a method of treating a subject in need of a non-syngeneic cell or tissue graft, the method comprising: (a) transplanting into a subject a dose of T cell depleted immature hematopoietic cells, wherein the T cell depleted immature hematopoietic cells comprise less than $5 \times 10^5$ $CD3^+$ T cells per kilogram body weight of the subject, and wherein the dose comprises at least about $5 \times 10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

According to an aspect of some embodiments of the present invention there is provided a method of treating a subject in need of an immature hematopoietic cell transplantation, the method comprising: (a) transplanting into a conditioned subject a dose of T cell depleted immature hematopoietic cells, wherein the T cell depleted immature hematopoietic cells comprise less than $5 \times 10^5$ CD3+ T cells per kilogram body weight of the subject, and wherein the dose comprises at least about $5 \times 10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

According to an aspect of some embodiments of the present invention there is provided a method of treating a subject in need of an immature hematopoietic cell transplantation, the method comprising: (a) conditioning a subject under a reduced intensity conditioning protocol, wherein the reduced intensity conditioning comprises a total body irradiation (TBI) and a chemotherapeutic agent; (b) transplanting into the subject a dose of T cell depleted immature hematopoietic cells, wherein the T cell depleted immature hematopoietic cells comprise less than $5 \times 10^5$ CD3+ T cells per kilogram body weight of the subject, and wherein the dose comprises at least about $5 \times 10^6$ CD34+ cells per kilogram body weight of the subject; and subsequently (c) administering to the subject a therapeutically effective amount of cyclophosphamide, wherein the therapeutically effective amount comprises 25-200 mg per kilogram body weight, thereby treating the subject.

According to an aspect of some embodiments of the present invention there is provided a method of inducing donor specific tolerance in a subject in need of a non-syngeneic cell or tissue graft, the method comprising: (a) transplanting into a subject a dose of T cell depleted immature hematopoietic cells obtained from a non-syngeneic donor, wherein the T cell depleted immature hematopoietic cells comprise less than $5 \times 10^5$ CD3$^+$ T cells per kilogram body weight of the subject, and wherein the dose comprises at least about $5 \times 10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby inducing donor specific tolerance in the subject.

According to some embodiments of the invention, the method further comprises conditioning the subject under reduced intensity conditioning prior to step (a).

According to some embodiments of the invention, the method further comprises conditioning the subject with in-vivo T cell debulking prior to step (a).

According to some embodiments of the invention, the dose of the T cell depleted immature hematopoietic cells comprises $5-40 \times 10^6$ CD34+ cells per kilogram body weight of the subject.

According to some embodiments of the invention, the dose of the T cell depleted immature hematopoietic cells comprises at least about $10 \times 10^6$ CD34+ cells per kilogram body weight of the subject.

According to some embodiments of the invention, the T cell depleted immature hematopoietic cells are selected from the group consisting of T cell depleted bone marrow cells, T cell depleted G-CSF mobilized peripheral blood progenitor cells, T cell depleted cord blood, purified CD34+ cells attained by positive selection from bone marrow and/or from G-CSF mobilized peripheral blood progenitor cells, and ex-vivo expanded CD34$^+$ cells.

According to some embodiments of the invention, the T cell depleted immature hematopoietic cells comprise less than $1 \times 10^6$ CD8$^+$ TCRα/β$^-$ cells per kilogram body weight of the subject.

According to some embodiments of the invention, the T cell depleted immature hematopoietic cells are obtained by T cell debulking.

According to some embodiments of the invention, the T cell debulking is effected by antibodies.

According to some embodiments of the invention, the antibodies are selected from the group consisting of an anti-CD8 antibody, an anti-CD4 antibody, an anti-CD3 antibody, an anti-CD2 antibody and an anti-TCRα/β antibody.

According to some embodiments of the invention, the antibodies comprise an anti-CD3 antibody.

According to some embodiments of the invention, the immature hematopoietic cells are treated by B cell debulking.

According to some embodiments of the invention, the B cell debulking is effected by an anti-CD19 antibody or by anti-CD20 antibody.

According to some embodiments of the invention, the T cell depleted immature hematopoietic cells are obtained from a non-syngeneic donor.

According to some embodiments of the invention, the non-syngeneic donor is allogeneic or xenogeneic with respect to the subject.

According to some embodiments of the invention, the allogeneic donor is selected from the group consisting of an HLA matched sibling, an HLA matched unrelated donor, an HLA haploidentical related donor and a donor displaying one or more disparate HLA determinants.

According to some embodiments of the invention, the subject is a human subject.

According to some embodiments of the invention, the in-vivo T cell debulking is effected by antibodies.

According to some embodiments of the invention, the antibodies comprise an anti-CD8 antibody, an anti-CD4 antibody, or both.

According to some embodiments of the invention, the antibodies comprise anti-thymocyte globulin (ATG) antibodies, anti-CD52 antibodies or anti-CD3 (OKT3®) antibodies.

According to some embodiments of the invention, the reduced intensity conditioning comprises a non-myeloablative conditioning.

According to some embodiments of the invention, the non-myeloablative conditioning comprises at least one of a total body irradiation (TBI), a total lymphoid irradiation (TLI), a chemotherapeutic agent and/or an antibody immunotherapy.

According to some embodiments of the invention, the TBI comprises a single or fractionated irradiation dose within the range of 1-7.5 Gy.

According to some embodiments of the invention, the TBI comprises a single or fractionated irradiation dose within the range of 1-3.5 Gy.

According to some embodiments of the invention, the TBI comprises a single or fractionated irradiation dose within the range of 2 Gy.

According to some embodiments of the invention, the TBI is effected in a single dose 2 days prior to step (b).

According to some embodiments of the invention, the chemotherapeutic agent comprises at least one of Busulfan, Fludarabine, Melphalan and Thiotepa.

According to some embodiments of the invention, the antibody comprises at least one of an anti-CD52 antibody, anti-thymocyte globulin (ATG) antibody or anti-CD3 (OKT3®) antibody.

According to some embodiments of the invention, the concentration of the cyclophosphamide is about 100-200 mg per kg body weight.

According to some embodiments of the invention, the concentration of the cyclophosphamide is about 100 mg per kg body weight.

According to some embodiments of the invention, the cyclophosphamide is administered in a single dose.

According to some embodiments of the invention, the cyclophosphamide is administered in two doses.

According to some embodiments of the invention, each of the two doses comprises a concentration of about 50 mg per kg body weight.

According to some embodiments of the invention, each of the two doses is administered on days 3 and 4 following step (a).

According to some embodiments of the invention, the subject has a malignant disease.

According to some embodiments of the invention, the malignant disease is a hematopoietic cancer.

According to some embodiments of the invention, the hematopoietic cancer comprises a leukemia or lymphoma.

According to some embodiments of the invention, the hematopoietic cancer is selected from the group consisting of acute lymphoblastic leukemia (ALL), acute myelocytic leukemia (AML), acute nonlymphoblastic leukemia (ANLL), Chronic lymphocytic leukemia (CLL), chronic myelocytic leukemia (CML), Hodgkin's Lymphoma, non-Hodgkin's Lymphoma, Extranodal natural killer/T-cell lymphoma, Cutaneous T-cell lymphoma, Enteropathy type T-cell lymphoma, Angioimmunoblastic T-cell lymphoma, Anaplastic large T/null-cell lymphoma, Subcutaneous panniculitis-like T-cell lymphoma, Unspecified T-cell lymphoma, Diffuse large B-cell lymphoma, B-cell chronic lymphocytic leukemia (B-CLL)/chronic lymphoid leukemia (CLL), Chronic lymphocytic leukemia/small lymphocytic lymphoma, Extranodal marginal zone B-cell lymphomas—mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Lymphoplasmocytic lymphoma, Primary mediastinal B-cell lymphoma and multiple myeloma.

According to some embodiments of the invention, the subject has a non-malignant disease.

According to some embodiments of the invention, the non-malignant disease is a genetic disease or disorder, an autoimmune disease or a metabolic disorder.

According to some embodiments of the invention, the non-malignant disease is selected from the group consisting of sickle cells disease, a congenital neutropenia, a thrombocytopenia, an aplastic anemia, a myelodysplastic syndrome, a monosomy 7, an osteopetrosis, a Gaucher's disease, a Hurler's disease, a metachromatic leukodystrophy, an adrenal leukodystrophy, a thalassemia, a congenital or genetically-determined hematopoietic abnormality, lupus, autoimmune hepatitis, celiac disease, type I diabetes mellitus, Grave's disease, Guillain-Barr syndrome, Myasthenia gravis, Rheumatoid arthritis, scleroderma and psoriasis.

According to some embodiments of the invention, the cell or tissue graft comprises immature hematopoietic cells.

According to some embodiments of the invention, the cell or tissue graft is selected from the group consisting of a liver, a pancreas, a spleen, a kidney, a heart, a lung, a skin, an intestine and a lymphoid/hematopoietic tissue or organ.

According to some embodiments of the invention, the cell or tissue graft is transplanted into the subject prior to, concomitantly with or following the transplanting the dose of T cell depleted immature hematopoietic cells into the subject.

According to some embodiments of the invention, the cell or tissue graft comprises a co-transplantation of several organs.

According to some embodiments of the invention, the cell or tissue graft and the T cell depleted immature hematopoietic cells are obtained from the same donor.

According to some embodiments of the invention, the conditioned subject has been conditioned under reduced intensity conditioning.

According to some embodiments of the invention, the reduced intensity conditioning is effected 1-10 days prior to the transplanting.

According to some embodiments of the invention, the conditioned subject has been conditioned with in-vivo T cell debulking.

According to some embodiments of the invention, the in-vivo T cell debulking is effected 4-7 days prior to the transplanting.

According to some embodiments of the invention, the chemotherapeutic agent comprises Fludarabine.

According to some embodiments of the invention, the Fludarabine is effected at a dose of 30 $mg/m^2/day$.

According to some embodiments of the invention, the Fludarabine is administered daily on days 3 to 7 prior to step (b).

According to some embodiments of the invention, the T cell depleted immature hematopoietic cells comprise T cell depleted G-CSF mobilized peripheral blood progenitor cells.

It will be appreciated that the present teachings can be used with other tolerance inducing protocols such as described in PCT publication Nos. WO 2001/49243, WO 2007/023491 and WO 2010/049935, which are herein incorporated by reference in their entirety.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1B are graphs illustrating durable engraftment of mismatched donor bone marrow (BM) following transplantation of 'mega dose' rigorously T cell depleted BM and posttranplantation cyclophosphamide. Mice were conditioned with T cell debulking (TCD), using anti-CD4 and anti-CD8 antibodies, on day −6, and by exposure to 2.0 Gy total body irradiation (TBI) on day −1. High dose Cyclophosphamide (CY, 100 mg/kg) was administered on days +3 and +4 post transplant. Donor type chimerism was evaluated 35 days (FIG. 1A) and 95 days (FIG. 1B) post transplant.

FIGS. 2A-2C are dot plot graphs illustrating a typical FACS chimerism analysis. FIG. 2C depicts that mixed chimerism was achieved in recipients that were transplanted with 'mega dose' ($25 \times 10^6$) rigorously T cell depleted BM and were treated with high dose CY. In contrast, recipient mice that received only the conditioning protocol (FIG. 2A) or which were inoculated with only $5 \times 10^6$ BM cells and CY did not exhibit donor type chimerism (FIG. 2B).

Figure 3:
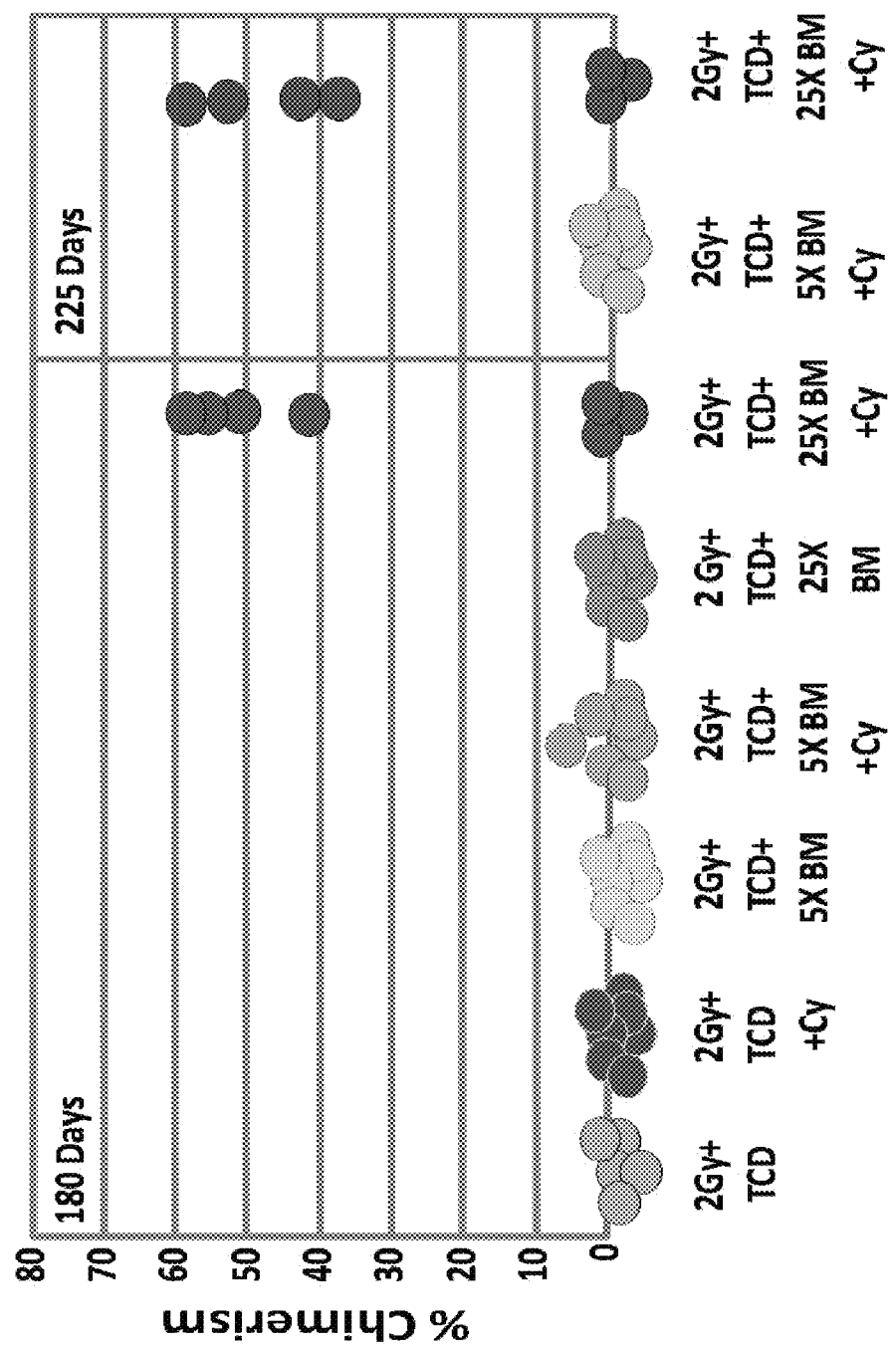

FIG. 3 is a graph illustrating durable mixed chimerism 180 and 225 days post transplant in recipient mice that were transplanted with 'mega dose' ($25 \times 10^6$) T cell depleted BM and were treated with high dose CY. Of note, mice which were inoculated with $5 \times 10^6$ T cell depleted BM and CY did not exhibit mixed chimerism.

Figure 4A:
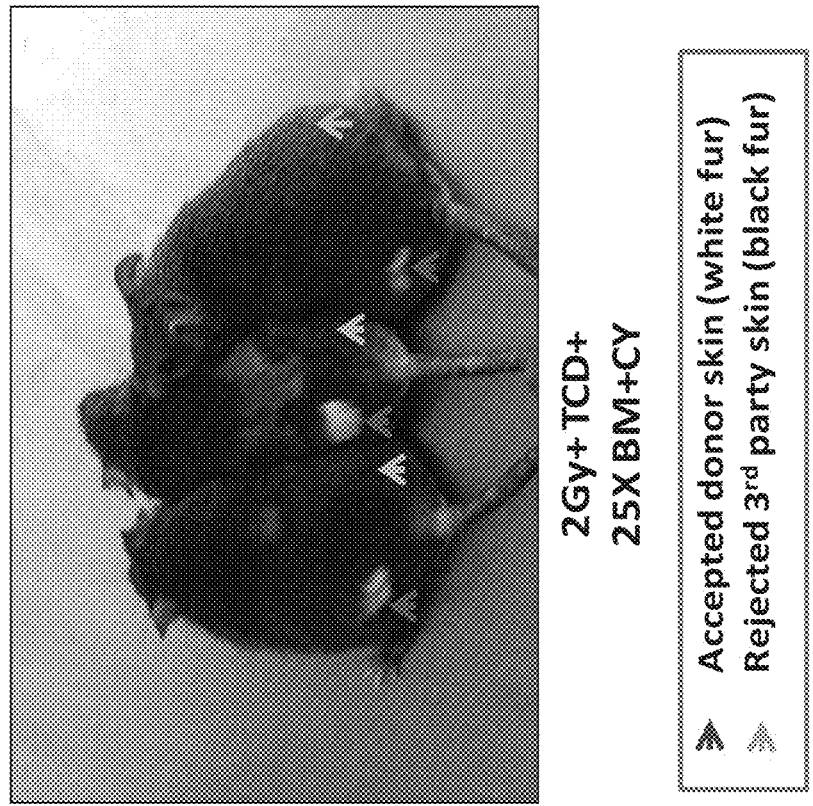
Figure 4B:
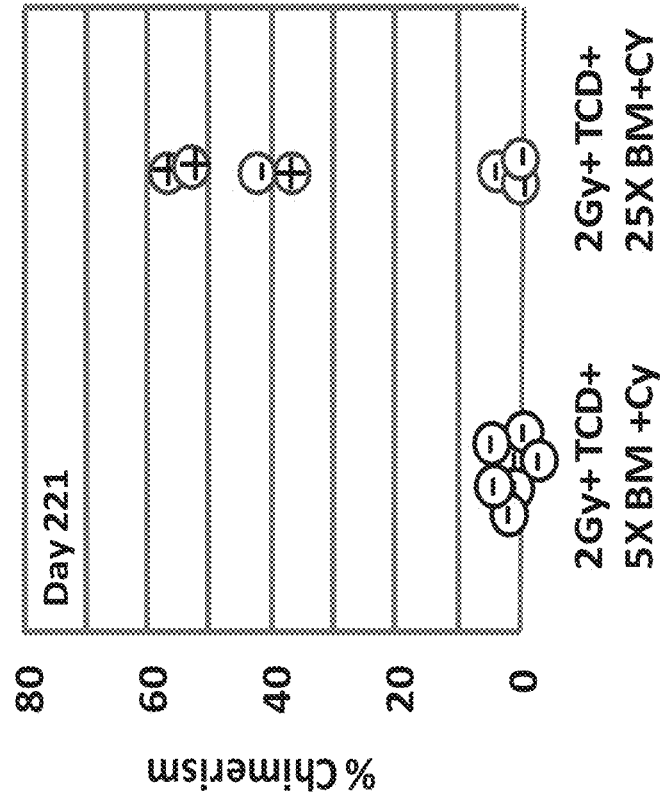

FIGS. 4A-4B illustrate the transplantation of donor type or $3^{rd}$ party skin grafts in chimeric mice. FIG. 4A is a graft illustrating acceptance (marked by "+") or rejection (marked by "−") of donor type (Balb/c) or $3^{rd}$ party (C57BL/6) skin grafts in recipients of regular dose ($5 \times 10^6$) or 'mega dose' ($25 \times 10^6$) T depleted BM, treated with high dose CY on days +3 and +4 post transplant. FIG. 4B is a photograph of donor type (Balb/c) skin graft (white fur) or $3^{rd}$ party (C57BL/6) skin graft (black fur) in recipients of 'mega dose' ($25 \times 10^6$) T depleted BM, treated with high dose CY on days +3 and +4 post transplant.

Figure 5:
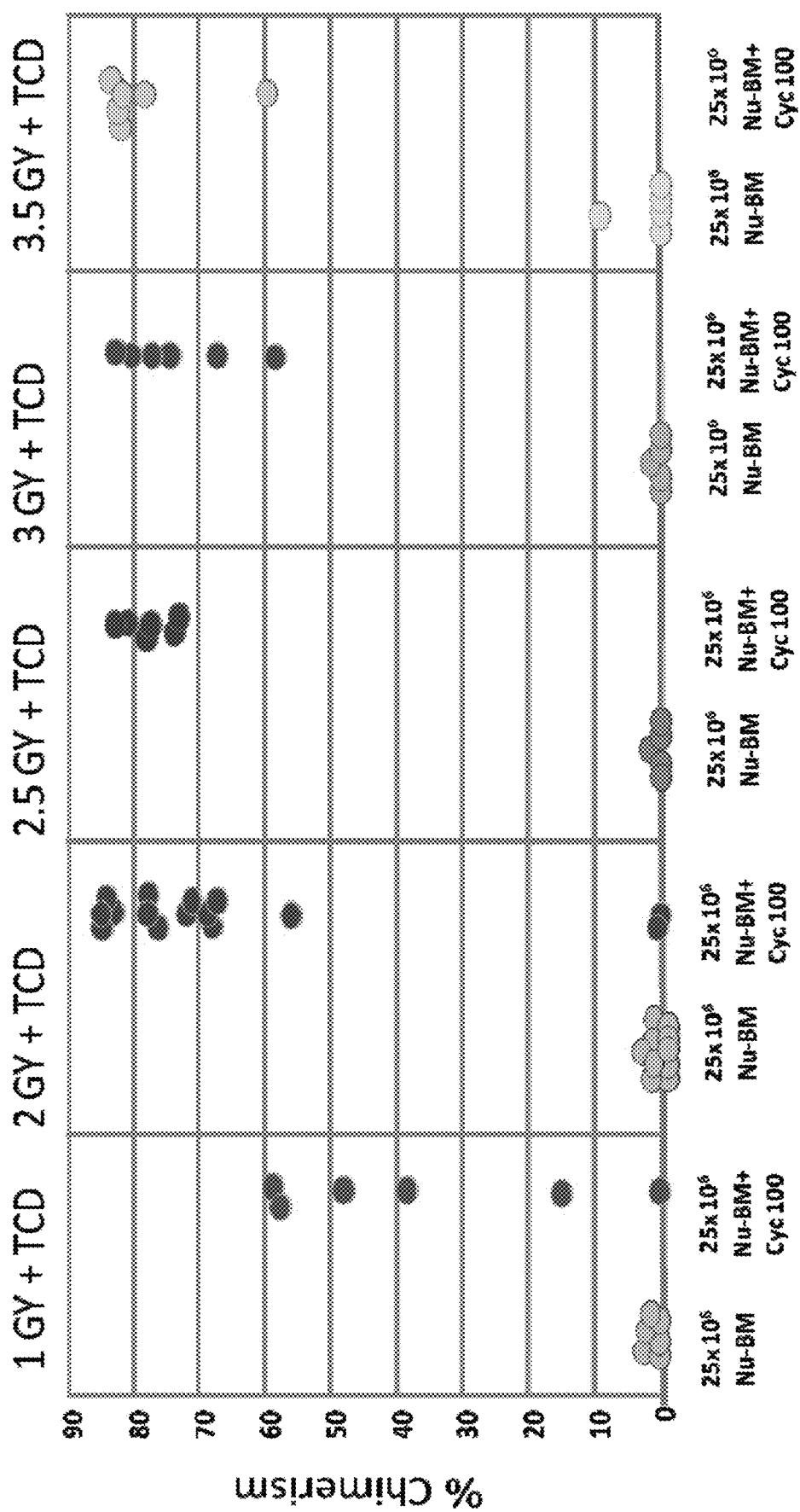

FIG. 5 is a graph illustrating the effect of different doses of irradiation on donor type chimerism in recipient mice of 'mega dose' ($25 \times 10^6$) T depleted BM and treated with high dose CY post transplant.

Figure 6:
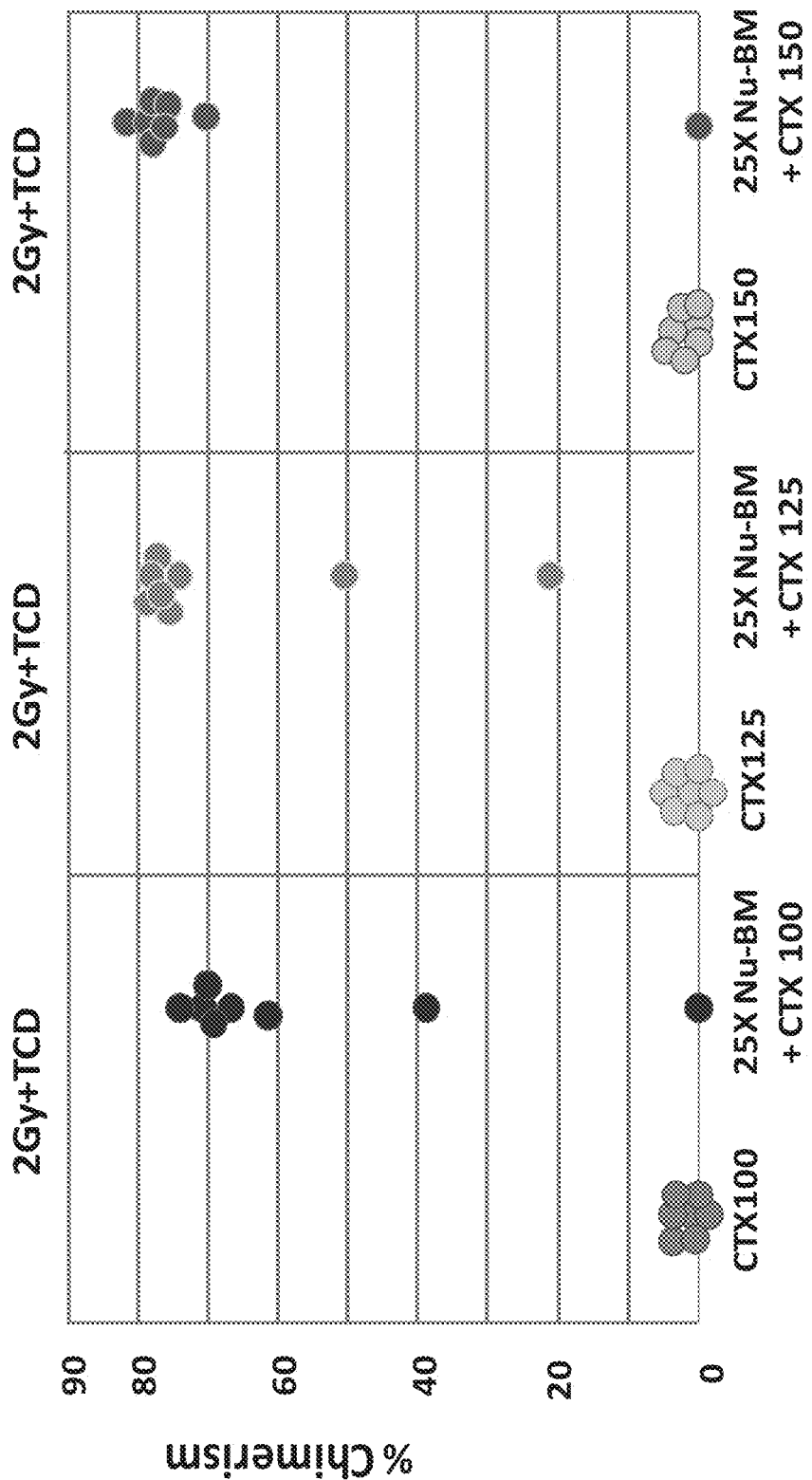

FIG. 6 is a graph illustrating the effect of increased doses of Cyclophosphamide (CY) on donor type chimerism in recipients of 'mega dose' ($25 \times 10^6$) T depleted BM and 2 Gy TBI.

Figure 7:
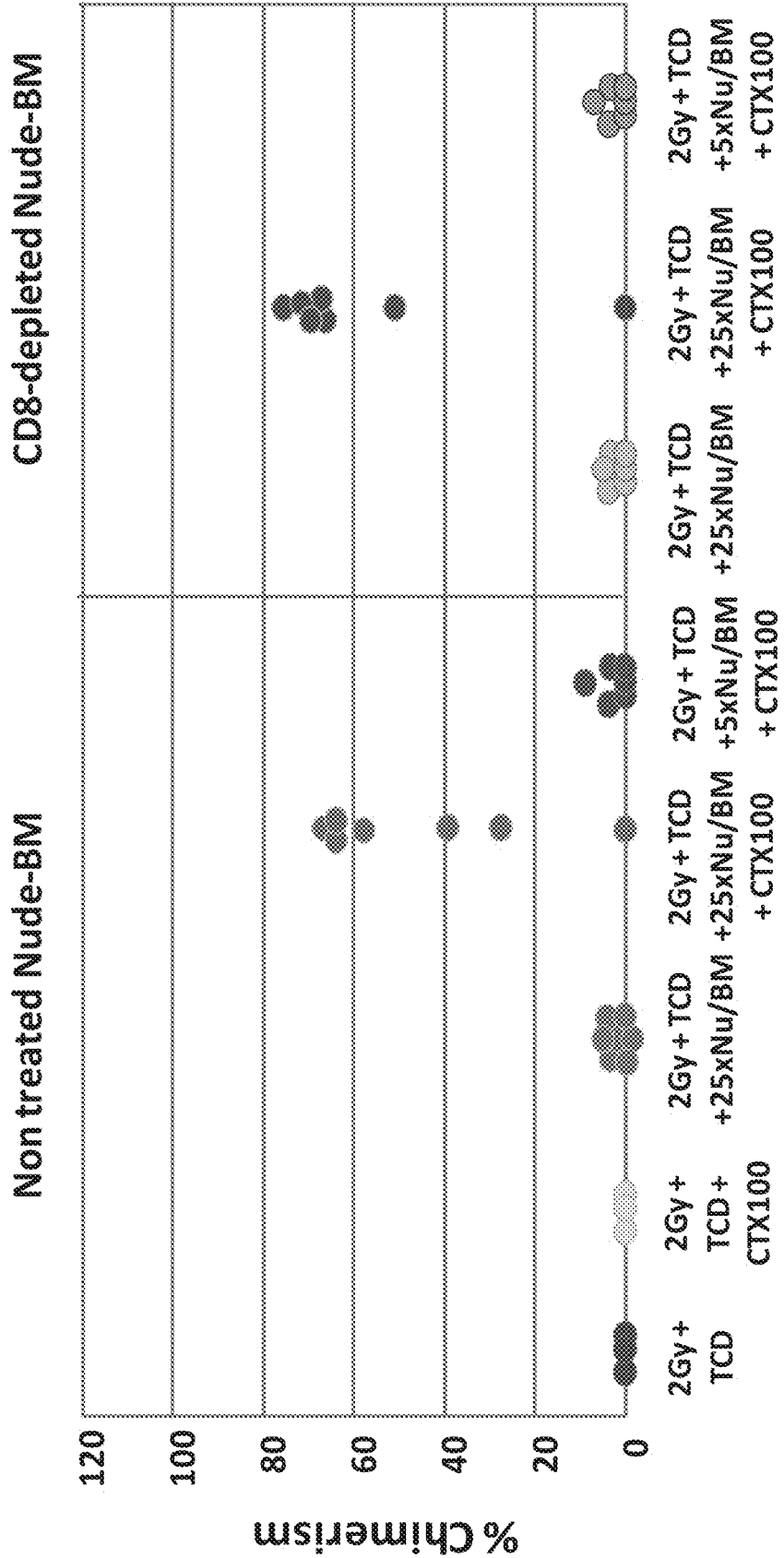

FIG. 7 is a graph illustrating engraftment of mismatched donor BM achieved by combining 'mega dose' CD8$^+$ T cell depleted BM and post transplant CY. Of note, the depletion of residual CD8$^+$ T cells from the BM preparation did not have any adverse impact on the level of chimerism achieved when combing 'mega dose' T cell depleted BM cells with post transplant CY.

DESCRIPTION OF SPECIFIC EMBODIMENTS OF THE INVENTION

The present invention, in some embodiments thereof, relates to a combination therapy for attaining a stable and long term cell or tissue transplantation.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Application of allogeneic hematopoietic stem cell transplantation (HSCT) has been limited by the lack of available HLA-matched donors within the family or in the international registries of unrelated volunteer donors. Conversely, virtually all patients in need for a transplant have a full-haplotype mismatched family donor.

The major obstacles to bone marrow transplantation from full-haplotype mismatched related donors were graft versus host disease (GVHD) and graft rejection.

The use of very large numbers of hematopoietic stem cells with minimal residual T cell contamination and an aggressive immunosuppressive and myeloablative regimen has resulted in high rates of engraftment with little severe GVHD. However, immune reconstitution has been delayed and incomplete after this approach and a significant rate of transplant related mortality (TRM) is caused by opportunistic infections.

While reducing the present invention to practice, the present inventors have uncovered that a successful engraftment of mismatched bone marrow can be achieved by transplantation of rigorously T cell depleted 'mega dose' bone marrow and subsequently administering to the subject a high-dose cyclophospamide early after transplantation.

The present inventors have shown that such a regimen requires only a short immunomyeloablative conditioning regimen. The present inventors have further shown that such a transplantation procedure leads to a long and stable chimerism and that tolerance has been achieved.

As is shown hereinbelow and in the Examples section which follows, the present inventors have uncovered through laborious experimentation that the combination of 'mega dose' T cell depleted bone marrow transplantation (TDBMT) and post transplant high dose cyclophosphamide (CY) allows for a durable engraftment of mismatched donor bone marrow (see FIGS. 1A-1B and 2A-2C). Durable mixed chimerism was exhibited for prolonged periods of time after transplantation (180 and 225 days post transplant in mice, see FIG. 3). Importantly, the combination of 'mega dose' TDBMT and high dose CY following transplantation allowed hematopoietic stem cell engraftment under reduced intensity conditioning (see FIG. 5) and resulted in tolerance induction, as indicated by acceptance of donor skin grafts (see FIG. 4B).

Thus, according to one aspect of the present invention there is provided a method of treating a subject in need of a non-syngeneic cell or tissue graft, the method comprising: (a) transplanting into a subject a dose of T cell depleted immature hematopoietic cells, wherein the T cell depleted immature hematopoietic cells comprise less than $5 \times 10^5$ CD3$^+$ T cells per kilogram body weight of the subject, and wherein the dose comprises at least about $5 \times 10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" or "subject in need thereof" refers to a mammal, preferably a human being, male or female at any age that is in need of a cell or tissue transplantation. Typically the subject is in need of cell or tissue transplantation (also referred to herein as recipient) due to a disorder or a pathological or undesired condition, state, or syndrome, or a physical, morphological or physiological abnormality which is amenable to treatment via cell or tissue transplantation.

According to an embodiment the subject is in need of tissue regeneration (solid or soft tissue) such as due to aging, trauma, wound or any pathological condition which results in loss of organ functionality.

According to one embodiment the subject has a malignant disease.

According to one embodiment the malignant disease is a hematopoietic cancer.

Exemplary hematopoietic cancers include, but are not limited to, acute lymphoblastic leukemia (ALL), T-cell acute lymphocytic leukemia (T-ALL), acute myelocytic leukemia (AML), acute nonlymphoblastic leukemia (ANLL), chronic lymphocytic leukemia (CLL), chronic myelocytic leukemia (CML), T-cell prolymphocytic leukemia, B-cell prolymphocytic leukemia, Juvenile myelomonocytic leukemia, Hodgkin's Lymphoma, non-Hodgkin's Lymphoma, Extranodal natural killer/T-cell lymphoma, Cutaneous T-cell lymphoma, Enteropathy type T-cell lymphoma, Angioimmunoblastic T-cell lymphoma, Anaplastic large T/null-cell lymphoma, Subcutaneous panniculitis-like T-cell lymphoma, Unspecified T-cell lymphoma, Diffuse large B-cell lymphoma (DLBCL), B-cell chronic lymphocytic leukemia (B-CLL)/chronic lymphoid leukemia (CLL), Chronic lymphocytic leukemia/small lymphocytic lymphoma, Extranodal marginal zone B-cell lymphomas—mucosa-associated lymphoid tissue lymphomas, Follicular lymphoma, Mantle cell lymphoma, Nodal marginal zone B-cell lymphoma, Burkitt lymphoma, Hairy cell leukemia, Primary central nervous system lymphoma, Splenic marginal zone B-cell lymphoma, Lymphoplasmocytic lymphoma, Primary mediastinal B-cell lymphoma, precursor T-cell leukemia/lymphoma, MALT lymphoma, Mycosis fungoides and multiple myeloma.

According to one embodiment the hematopoietic cancer comprises a leukemia or a lymphoma.

According to one embodiment the subject has a non-malignant disease.

According to one embodiment the non-malignant disease is a genetic disease or disorder, an autoimmune disease or a metabolic disorder.

Exemplary non-malignant diseases include, but are not limited to, severe combined immunodeficiency syndromes (SCID), sickle cell disease (sickle cell anemia), congenital neutropenia, thrombocytopenia, aplastic anemia (e.g. severe aplastic anemia), myelodysplastic syndrome, monosomy 7, osteopetrosis, Gaucher's disease, Hurler's disease, metachromatic leukodystrophy, adrenal leukodystrophy, thalassemia, congenital or genetically-determined hematopoietic abnormality, adenosine deaminase (ADA), lupus, autoimmune hepatitis, celiac disease, type I diabetes mellitus, Grave's disease, Guillain-Barr syndrome, Myasthenia gravis, Rheumatoid arthritis, scleroderma and psoriasis.

According to one embodiment the subject of the present invention may suffer from any of a cardiovascular disease, a rheumatoid disease, a glandular disease, a gastrointestinal disease, a cutaneous disease, a hepatic disease, a neurological disease, a muscular disease, a nephric disease, a connective tissue disease, a systemic disease and/or a disease related to reproduction, treatable by cell or tissue transplantation.

As used herein, the phrase "cell or tissue graft" refers to a bodily cell (e.g. a single cell or a group of cells) or tissue (e.g. solid tissues or soft tissues, which may be transplanted in full or in part). Exemplary tissues which may be transplanted according to the present teachings include, but are not limited to, liver, pancreas, spleen, kidney, heart, lung, skin, intestine and lymphoid/hematopoietic tissues (e.g. lymph node, Peyer's patches, thymus or bone marrow). Exemplary cells which may be transplanted according to the present teachings include, but are not limited to, immature hematopoietic cells including stem cells. The present invention also contemplates transplantation of whole organs, such as for example, kidney, heart, lung, liver, pancreas or spleen.

According to one embodiment, the cell or tissue graft comprises immature hematopoietic cells.

According to one embodiment, the method is effected using a cell or tissue, which is non-syngeneic with the subject.

Depending on the application, the method may be effected using a cell or tissue graft which is allogeneic or xenogeneic with the subject.

As used herein, the term "allogeneic" refers to a cell or tissue which is derived from a donor who is of the same species as the subject, but which is substantially non-clonal with the subject. Typically, outbred, non-zygotic twin mammals of the same species are allogeneic with each other. It will be appreciated that an allogeneic donor may be HLA identical or HLA non-identical (i.e. displaying one or more disparate HLA determinants) with respect to the subject.

According to one embodiment, the allogeneic donor is an HLA matched sibling, an HLA matched unrelated donor, an HLA haploidentical related donor or a donor displaying one or more disparate HLA determinants.

As used herein, the term "xenogeneic" refers to a cell or tissue which substantially expresses antigens of a different species relative to the species of a substantial proportion of the lymphocytes of the subject. Typically, outbred mammals of different species are xenogeneic with each other.

The present invention envisages that xenogeneic cells or tissues are derived from a variety of species such as, but not limited to, bovines (e.g., cow), equines (e.g., horse), porcines (e.g. pig), ovids (e.g., goat, sheep), felines (e.g., *Felis domestica*), canines (e.g., *Canis domestica*), rodents (e.g., mouse, rat, rabbit, guinea pig, gerbil, hamster) or primates (e.g., chimpanzee, rhesus monkey, macaque monkey, marmoset).

Cells or tissues of xenogeneic origin (e.g. porcine origin) are preferably obtained from a source which is known to be free of zoonoses, such as porcine endogenous retroviruses. Similarly, human-derived cells or tissues are preferably obtained from substantially pathogen-free sources.

According to an embodiment of the present invention, both the subject and the donor are humans.

Depending on the application and available sources, the cell or tissue graft of the present invention may be obtained from a prenatal organism, postnatal organism, an adult or a cadaver donor. Moreover, depending on the application needed, the cell or tissue graft may be naïve or genetically modified. Determination of the type of cell or tissue graft to be used is well within the ability of one of ordinary skill in the art. Furthermore, any method known in the art may be employed to obtain a cell or tissue graft (e.g. for transplantation).

As mentioned, a dose of T cell depleted hematopoietic cell or tissue comprising immature hematopoietic cells (including e.g. $CD34^+$), are transplanted into a subject.

According to one embodiment, the T cell depleted immature hematopoietic cells are non-syngeneic (e.g. allogeneic or xenogeneic) with the subject.

According to one embodiment, the T cell depleted immature hematopoietic cells and the cell or tissue graft are syngeneic (e.g. obtained from the same donor).

As used herein the phrase "immature hematopoietic cells" refers to a hematopoietic tissue or cell preparation comprising precursor hematopoietic cells. Such tissue/cell preparation includes or is derived from a biological sample, for example, bone marrow, mobilized peripheral blood (e.g. mobilization of CD34 cells to enhance their concentration), cord blood (e.g. umbilical cord), fetal liver, yolk sac and/or placenta. Additionally, purified CD34+ cells or other hematopoietic stem cells such as CD131+ cells can be used in accordance with the present teachings, either with or without ex-vivo expansion.

According to one embodiment, the immature hematopoietic cells comprise T cell depleted immature hematopoietic cells.

As used herein the phrase "T cell depleted immature hematopoietic cells" refers to a population of hematopoietic cells which are depleted of T lymphocytes. The T cell depleted immature hematopoietic cells, may include e.g. CD34+, CD33+ and/or CD56+ cells. The T cell depleted immature hematopoietic cells may be depleted of CD3+ cells, CD2+ cells, CD8+ cells, CD4+ cells, $\alpha/\beta$ T cells and/or $\gamma/\delta$ T cells.

According to one embodiment, the immature hematopoietic cells comprise T cell depleted G-CSF mobilized blood cells enriched for CD34+ immature hematopoietic cells.

According to one embodiment, the immature hematopoietic cells are depleted of CD3+ T cells.

According to an embodiment, the T cell depleted immature hematopoietic cells comprise less than $50 \times 10^5$ CD3+ T cells, $40 \times 10^5$ CD3+ T cells, $30 \times 10^5$ CD3+ T cells, $20 \times 10^5$ CD3+ T cells, $15 \times 10^5$ CD3+ T cells, $10 \times 10^5$ CD3+ T cells, $9 \times 10^5$ CD3+ T cells, $8 \times 10^5$ CD3+ T cells, $7 \times 10^5$ CD3+ T cells, $6 \times 10^5$ CD3+ T cells, $5 \times 10^5$ CD3+ T cells, $4 \times 10^5$ CD3+ T cells, $3 \times 10^5$ CD3+ T cells, $2 \times 10^5$ CD3+ T cells or $1 \times 10^5$ CD3+ T cells per kilogram body weight of the subject.

According to a specific embodiment, the T cell depleted immature hematopoietic cells comprise less than $5 \times 10^5$ CD3+ T cells per kilogram body weight of the subject.

According to a specific embodiment the T cell depleted immature hematopoietic cells comprise less than $20 \times 10^5$ CD3+ T cells but more than 10 CD3+ T cells.

According to an embodiment, the T cell depleted immature hematopoietic cells comprise at least $1 \times 10^3$-$1 \times 10^5$ CD3+ T cells.

According to one embodiment, the immature hematopoietic cells are depleted of CD8+ cells.

According to an embodiment, the T cell depleted immature hematopoietic cells comprise less than $1 \times 10^4$-$4 \times 10^5$ CD8+ cells per kilogram body weight of the subject.

According to an embodiment, the T cell depleted immature hematopoietic cells comprise less than $50 \times 10^5$ CD8+ cells, $25 \times 10^5$ CD8+ cells, $15 \times 10^5$ CD8+ cells, $10 \times 10^5$ CD8+ cells, $9 \times 10^5$ CD8+ cells, $8 \times 10^5$ CD8+ cells, $7 \times 10^5$ CD8+ cells, $6 \times 10^5$ CD8+ cells, $5 \times 10^5$ CD8+ cells, $4 \times 10^5$ CD8+ cells, $3 \times 10^5$ CD8+ cells, $2 \times 10^5$ CD8+ cells, $1 \times 10^5$ CD8+ cells, $9 \times 10^4$ CD8+ cells, $8 \times 10^4$ CD8+ cells, $7 \times 10^4$ CD8+ cells, $6 \times 10^4$ CD8+ cells, $5 \times 10^4$ CD8+ cells, $4 \times 10^4$ CD8+ cells, $3 \times 10^4$ CD8+ cells, $2 \times 10^4$ CD8+ cells or $1 \times 10^4$ CD8+ cells per kilogram body weight of the subject.

According to a specific embodiment, the T cell depleted immature hematopoietic cells comprise less than $4 \times 10^5$ CD8+ cells per kilogram body weight of the subject.

According to a specific embodiment the T cell depleted immature hematopoietic cells comprise less than $4 \times 10^5$ CD8+ cells but more than 10 CD8+ cells.

According to an embodiment, the T cell depleted immature hematopoietic cells comprise less than $1 \times 10^6$ CD8+ TCR$\alpha$/$\beta$⁻ cells per kilogram body weight of the subject.

According to an embodiment, the T cell depleted immature hematopoietic cells comprise less than $1 \times 10^6$ CD8+ TCR$\alpha$/$\beta$⁻ cells, $0.5 \times 10^6$ CD8+ TCR$\alpha$/$\beta$⁻ cells, $1 \times 10^5$ CD8+ TCR$\alpha$/$\beta$⁻ cells, $0.5 \times 10^5$ CD8+ TCR$\alpha$/$\beta$⁻ cells, $1 \times 10^4$ CD8+ TCR$\alpha$/$\beta$⁻ cells, $0.5 \times 10^4$ CD8+ TCR$\alpha$/$\beta$⁻ cells, $1 \times 10^3$ CD8+ TCR$\alpha$/$\beta$⁻ cells or $0.5 \times 10^3$ CD8+ TCR$\alpha$/$\beta$⁻ cells per kilogram body weight of the subject.

According to a specific embodiment, the T cell depleted immature hematopoietic cells comprise less than $1 \times 10^6$ CD8+ TCR$\alpha$/$\beta$⁻ cells per kilogram body weight of the subject.

According to a specific embodiment the T cell depleted immature hematopoietic cells comprise less than $1 \times 10^6$ CD8+ TCR$\alpha$/$\beta$⁻ cells but more than 10 CD8+ TCR$\alpha$/$\beta$⁻ cells.

According to one embodiment, the immature hematopoietic cells are depleted of B cells.

According to an embodiment, the immature hematopoietic cells are depleted of B cells (CD19+ and/or CD20+ B cells).

According to an embodiment, the immature hematopoietic cells comprise less than $50 \times 10^5$ B cells, $40 \times 10^5$ B cells, $30 \times 10^5$ B cells, $20 \times 10^5$ B cells, $10 \times 10^5$ B cells, $9 \times 10^5$ B cells, $8 \times 10^5$ B cells, $7 \times 10^5$ B cells, $6 \times 10^5$ B cells, $5 \times 10^5$ B cells, $4 \times 10^5$ B cells, $3 \times 10^5$ B cells, $2 \times 10^5$ B cells or $1 \times 10^5$ B cells per kilogram body weight of the subject.

According to a specific embodiment, the immature hematopoietic cells comprise less than $4 \times 10^5$ B cells per kilogram body weight of the subject. According to a specific embodiment the immature hematopoietic cells comprise less than $50 \times 10^5$ B cells but more than 10 B cells.

Depletion of T cells, e.g. CD3+, CD2+, TCR$\alpha$/$\beta$+, CD4+ and/or CD8+ cells, or B cells, e.g. CD19+ and/or CD20+ cells, may be carried out using any method known in the art, such as by eradication (e.g. killing) with specific antibodies or by affinity based purification e.g. such as by the use of magnetic cell separation techniques, FACS sorter and/or capture ELISA labeling.

Such methods are described herein and in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 1992). For example, cells can be sorted by, for example, flow cytometry or FACS. Thus, fluorescence activated cell sorting (FACS) may be used and may have varying degrees of color channels, low angle and obtuse light scattering detecting channels, and impedance channels. Any ligand-dependent separation techniques known in the art may be used in conjunction with both positive and negative separation techniques that rely on the physical properties of the cells rather than antibody affinity, including but not limited to elutriation and density gradient centrifugation.

Other methods for cell sorting include, for example, panning and separation using affinity techniques, including those techniques using solid supports such as plates, beads and columns. Thus, biological samples may be separated by "panning" with an antibody attached to a solid matrix, e.g. to a plate.

Alternatively, cells may be sorted/separated by magnetic separation techniques, and some of these methods utilize magnetic beads. Different magnetic beads are available from a number of sources, including for example, Dynal (Norway), Advanced Magnetics (Cambridge, Mass., U.S.A.), Immuncon (Philadelphia, U.S.A.), Immunotec (Marseille, France), Invitrogen, Stem cell Technologies (U.S.A) and Cellpro (U.S.A). Alternatively, antibodies can be biotinylated or conjugated with digoxigenin and used in conjunction with avidin or anti-digoxigenin coated affinity columns.

According to an embodiment, different depletion/separation methods can be combined, for example, magnetic cell sorting can be combined with FACS, to increase the separation quality or to allow sorting by multiple parameters.

According to one embodiment, the T cell depleted immature hematopoietic cells are obtained by T cell debulking (TCD).

T cell debulking may be effected using antibodies, including e.g. anti-CD8 antibodies, anti-CD4 antibodies, anti-CD3 antibodies, anti-CD2 antibodies, anti-TCRα/β antibodies and/or anti-TCRγ/δ antibodies.

According to one embodiment, depletion of B cells is effected by B cell debulking.

B cell debulking may be effected using antibodies, including e.g. anti-CD19 or anti-CD20 antibodies. Alternatively, debulking in-vivo of B cells can be attained by infusion of anti-CD20 antibodies.

Alternatively, positive selection of CD34+ or CD131+ stem cells may be carried out using e.g. magnetic cell separation techniques, FACS sorter and/or capture ELISA labeling as described in further detail above.

As mentioned, T cell or B cell debulking may be effected in-vitro or in-vivo (e.g. in a donor prior to acquiring immature hematopoietic cells therefrom).

According to one embodiment, the T cell depleted immature hematopoietic cells (e.g. comprising CD34+ cells) comprise T cell depleted bone marrow cells, T cell depleted mobilized peripheral blood progenitor cells (e.g. mobilized by G-CSF), T cell depleted cord blood/fetal liver/yolk sac and/or, purified CD34$^+$ cells (harvested from all the sources mentioned above e.g. from bone marrow and/or from G-CSF mobilized peripheral blood progenitor cells) and selected by positive selection (e.g. with magnetic beads using an anti-CD34 antibody). In addition purified CD34$^+$ cells expanded ex-vivo to increase cell numbers are also contemplated by the present methods.

According to an embodiment of the present invention, the subject is administered with a dose of T cell depleted immature hematopoietic cells comprising at least about, $4 \times 10^6$, $4.5 \times 10^6$, $5 \times 10^6$, $5.5 \times 10^6$, $6 \times 10^6$, $6.5 \times 10^6$, $7 \times 10^6$, $7.5 \times 10^6$, $8 \times 10^6$, $8.5 \times 10^6$, $9 \times 10^6$, $9.5 \times 10^6$, $10 \times 10^6$, $12.5 \times 10^6$, $15 \times 10^6$, $20 \times 10^6$, $25 \times 10^6$, $30 \times 10^6$, $35 \times 10^6$, $40 \times 10^6$, $45 \times 10^6$, $50 \times 10^6$, $60 \times 10^6$, $70 \times 10^{6'}$ $80 \times 10^6$, $90 \times 10^6$ CD34+ cells per kilogram body weight.

According to a specific embodiment, the subject is administered a dose of T cell depleted immature hematopoietic cells comprising at least about $10 \times 10^6$ CD34+ cells per kilogram body weight.

According to a specific embodiment, the subject is administered a dose of T cell depleted immature hematopoietic cells comprising at least about $5 \times 10^6$ CD34+ cells per kilogram body weight.

According to one embodiment, the subject is administered a dose of T cell depleted immature hematopoietic cells comprising a range of about $4\text{-}30 \times 10^6$, $4\text{-}40 \times 10^6$, $4\text{-}50 \times 10^6$, $4\text{-}60 \times 10^6$, $4\text{-}70 \times 10^6$, $4\text{-}80 \times 10^6$, $4\text{-}90 \times 10^6$, $4\text{-}100 \times 10^6$, $5\text{-}10 \times 10^6$, $5\text{-}20 \times 10^6$, $5\text{-}30 \times 10^6$, $5\text{-}40 \times 10^6$, $5\text{-}50 \times 10^6$, $5\text{-}60 \times 10^6$, $5\text{-}70 \times 10^6$, $5\text{-}80 \times 10^6$, $5\text{-}90 \times 10^6$, $5\text{-}100 \times 10^6$, $10\text{-}20 \times 10^6$, $10\text{-}30 \times 10^6$, $10\text{-}40 \times 10^6$, $10\text{-}50 \times 10^6$, $10\text{-}60 \times 10^6$, $10\text{-}70 \times 10^6$, $10\text{-}80 \times 10^6$, $10\text{-}90 \times 10^6$, $10\text{-}100 \times 10^6$, $20\text{-}30 \times 10^6$, $20\text{-}40 \times 10^6$, $20\text{-}50 \times 10^6$, $20\text{-}60 \times 10^6$, $20\text{-}70 \times 10^6$, $20\text{-}80 \times 10^6$, $20\text{-}90 \times 10^6$, $20\text{-}100 \times 10^6$, $30\text{-}40 \times 10^6$, $30\text{-}50 \times 10^6$, $30\text{-}60 \times 10^6$, $30\text{-}70 \times 10^6$, $30\text{-}80 \times 10^6$, $30\text{-}90 \times 10^6$, $30\text{-}100 \times 10^6$, $40\text{-}50 \times 10^6$, $40\text{-}60 \times 10^6$, $40\text{-}70 \times 10^6$, $40\text{-}80 \times 10^6$, $40\text{-}90 \times 10^6$, $40\text{-}100 \times 10^6$, $50\text{-}60 \times 10^6$, $50\text{-}70 \times 10^6$, $50\text{-}80 \times 10^6$, $50\text{-}90 \times 10^6$, $50\text{-}100 \times 10^6$, $60\text{-}70 \times 10^6$, $60\text{-}80 \times 10^6$, $60\text{-}90 \times 10^6$, $60\text{-}100 \times 10^6$, $70\text{-}80 \times 10^6$, $70\text{-}90 \times 10^6$, $70\text{-}100 \times 10^6$, $80\text{-}90 \times 10^6$, $80\text{-}100 \times 10^6$ CD34+ cells per kilogram body weight of the subject.

According to a specific embodiment, the subject is administered a dose of T cell depleted immature hematopoietic cells comprising a range of about $5\text{-}40 \times 10^6$ CD34+ cells per kilogram body weight.

The T cell depleted immature hematopoietic cells of the present invention may be transplanted into a recipient using any method known in the art for cell transplantation, such as but not limited to, cell infusion (e.g. I.V.), via an intraperitoneal route or via an intrabone route.

As mentioned, the subject of the instant invention may further be transplanted with a cell or tissue graft (e.g. liver, pancreas, spleen, kidney, heart, lung, skin, intestine and/or lymphoid/hematopoietic tissues).

Transplanting the cell or tissue into the subject may be effected in numerous ways, depending on various parameters, such as, for example, the cell or tissue type; the type, stage or severity of the recipient's disease (e.g. organ failure); the physical or physiological parameters specific to the subject; and/or the desired therapeutic outcome.

Transplanting a cell or tissue graft of the present invention may be effected by transplanting the cell or tissue graft into any one of various anatomical locations, depending on the application. The cell or tissue graft may be transplanted into a homotopic anatomical location (a normal anatomical location for the transplant), or into an ectopic anatomical location (an abnormal anatomical location for the transplant). Depending on the application, the cell or tissue graft may be advantageously implanted under the renal capsule, or into the kidney, the testicular fat, the sub cutis, the omentum, the portal vein, the liver, the spleen, the heart cavity, the heart, the chest cavity, the lung, the skin, the pancreas and/or the intra abdominal space.

For example, a liver tissue according to the present teachings may be transplanted into the liver, the portal vein, the renal capsule, the sub-cutis, the omentum, the spleen, and the intra-abdominal space. Transplantation of a liver into various anatomical locations such as these is commonly practiced in the art to treat diseases amenable to treatment via hepatic transplantation (e.g. hepatic failure). Similarly, transplanting a pancreatic tissue according to the present invention may be advantageously effected by transplanting the tissue into the portal vein, the liver, the pancreas, the testicular fat, the sub-cutis, the omentum, an intestinal loop (the subserosa of a U loop of the small intestine) and/or the intra-abdominal space. Transplantation of pancreatic tissue may be used to treat diseases amenable to treatment via pancreatic transplantation (e.g. diabetes). Likewise, transplantation of tissues such as a kidney, a heart, a lung or skin tissue may be carried out into any anatomical location described above for the purpose of treating recipients suffering from, for example, renal failure, heart failure, lung failure or skin damage (e.g., burns).

Optionally, when transplanting a cell or tissue graft of the present invention into a subject having a defective organ, it may be advantageous to first at least partially remove the failed organ from the subject so as to enable optimal development of the transplant, and structural/functional integration thereof with the anatomy/physiology of the subject.

The method of the present invention also envisions co-transplantation of several organs (e.g. heart and lung, liver and spleen, pancreas and bone marrow e.g. hematopoietic stem cells, kidney and bone marrow e.g. hematopoietic stem cells, etc.) in case the subject may be beneficially affected by such a procedure.

According to one embodiment, the co-transplantation comprises transplantation of immature hematopoietic cells and a solid tissue/organ or a number of solid organs/tissues.

According to one embodiment, the immature hematopoietic cells and the solid organ are obtained from the same donor.

According to one embodiment, the cell or tissue graft (e.g. solid organ) is transplanted into the subject prior to, concomitantly with or following transplanting of the T cell depleted immature hematopoietic cells (e.g. comprising CD34+ cells) into the subject.

Following transplantation of the cell or tissue graft into the subject, it is advisable, according to standard medical practice, to monitor the growth functionality and immuno-compatability of the organ according to any one of various standard art techniques. For example, the functionality of a pancreatic tissue transplant may be monitored following transplantation by standard pancreas function tests (e.g. analysis of serum levels of insulin). Likewise, a liver tissue transplant may be monitored following transplantation by standard liver function tests (e.g. analysis of serum levels of albumin, total protein, ALT, AST, and bilirubin, and analysis of blood-clotting time). Structural development of the cell or tissue graft may be monitored via computerized tomography, or ultrasound imaging.

Regardless of the transplant type, in order to reduce, by at least about 30%, 40%, 50%, 60%, 70%, 80%, 90% or 95%, or preferably avoid graft rejection and/or graft versus host disease (GVHD), the present invention contemplates post transplant administration of cyclophosphamide.

According to one embodiment, the present invention further contemplates administration of cyclophosphamide prior to transplantation (e.g. on days 4, 3 or 2 prior to transplantation, i.e. T-4, -3 or -2) in addition to the administration following transplantation as described herein.

Of note, the date of transplantation (of the cell or tissue graft) is considered T=zero.

As used herein, the term "cyclophosphamide" refers to the nitrogen mustard alkylating agent which specifically adds an alkyl group ($C_nH_{2n+1}$) to DNA (also known as cytophosphane). In a specific embodiment, the cyclophosphamide refers to the molecular formula $C_7H_{15}C_{12}N_2O_2P.H_2O$ and the chemical name 2-[bis(2-chloroethyl)amino]tetrahydro-2H-1,3,2-oxazaphosphorine 2-oxide monohydrate. Cyclophosphamide is commercially available from e.g. Zydus (German Remedies), Roxane Laboratories Inc-Boehringer Ingelheim, Bristol-Myers Squibb Co—Mead Johnson and Co, and Pfizer—Pharmacia & Upjohn, under the brand names of Endoxan, Cytoxan, Neosar, Procytox and Revimmune.

A therapeutically effective amount of cyclophosphamide is typically administered to the subject following transplantation of the cell or tissue graft.

Without being bound to theory, a therapeutically effective amount is an amount of cyclophosphamide efficient for killing activated donor or host alloreactive T cells without being toxic to the subject.

For example, in case of cell or tissue graft, the therapeutic effective amount of cyclophosphamide comprises about 1-25 mg, 1-50 mg, 1-75 mg, 1-100 mg, 1-250 mg, 1-500 mg, 1-750 mg, 1-1000 mg, 5-50 mg, 5-75 mg, 5-100 mg, 5-250 mg, 5-500 mg, 5-750 mg, 5-1000 mg, 10-50 mg, 10-75 mg, 10-100 mg, 10-250 mg, 10-500 mg, 10-750 mg, 10-1000 mg, 25-50 mg, 25-75 mg, 25-100 mg, 25-125 mg, 25-200 mg, 25-300 mg, 25-400 mg, 25-500 mg, 25-750 mg, 25-1000 mg, 50-75 mg, 50-100 mg, 50-125 mg, 50-150 mg, 50-175 mg, 50-200 mg, 50-250 mg, 50-500 mg, 50-1000 mg, 75-100 mg, 75-125 mg, 75-150 mg, 75-250 mg, 75-500 mg, 75-1000 mg, 100-125 mg, 100-150 mg, 100-200 mg, 100-300 mg, 100-400 mg, 100-500 mg, 100-1000 mg, 125-150 mg, 125-250 mg, 125-500 mg, 125-1000 mg, 150-200 mg, 150-300 mg, 150-500 mg, 150-1000 mg, 200-300 mg, 200-400 mg, 200-500 mg, 200-750 mg, 200-1000 mg, 250-500 mg, 250-750 mg, 250-1000 mg per kilogram body weight of the subject.

According to a specific embodiment, the therapeutic effective amount of cyclophosphamide is about 25-200 mg per kilogram body weight of the subject.

As illustrated in the Examples section which follows, the present inventors have shown that administration of two doses of cyclophosphamide post transplant (on days 3 and 4 post transplant) allows for a durable engraftment and tolerance of 'mega dose' T cell depleted mismatched donor bone marrow.

According to one embodiment, cyclophosphamide is administered in a single dose.

According to one embodiment, cyclophosphamide is administered in multiple doses, e.g. in 2, 3, 4, 5 doses or more.

According to a specific embodiment, cyclophosphamide is administered in two doses.

According to one embodiment, cyclophosphamide is administered daily such as once a day or twice a day.

The dose of each cyclophosphamide administration may comprise about 5 mg, 7.5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 350 mg, 400 mg, 450 mg or 500 mg per kilogram body weight of the subject.

According to a specific embodiment, the dose of cyclophosphamide is 50 mg per kilogram body weight of the subject.

As mentioned, cyclophosphamide is administered post transplantation. Thus, for example, cyclophosphamide may be administered to the subject 1, 2, 3, 4, 5, 6, 7, 8, 9, 10 days or more post transplant (i.e., T+1, +2, +3, +4, +5, +6, +7, +8, +9, +10).

According to a specific embodiment, cyclophosphamide is administered to the subject in two doses 3 and 4 days post transplant.

According to an embodiment, cyclophosphamide is administered prior to transplantation and post transplantation. Thus, for example, cyclophosphamide may be administered to the subject 3 days prior to transplantation (T−3) and then post transplantation (e.g. on days T+3, +4, etc.).

The number of administrations and the therapeutically effective amount of cyclophosphamide may be adjusted as needed taking into account the type of transplantation and the subject's response to the regimen. Determination of the number of administrations and the therapeutically effective amount is well within the capability of those skilled in the art, especially in light of the detailed disclosure provided herein. In order to facilitate engraftment of the cell or tissue graft, the method may further advantageously comprise conditioning the subject with an additional immunosuppressive drug and/or immunosuppressive irradiation prior to, concomitantly with or following transplantation of the cell or tissue graft.

It will be appreciated that in situations in which the cell or tissue graft (e.g. solid organ) is transplanted prior to the T cell depleted immature hematopoietic cells, it is advisable to use general immune suppressive agents (e.g. cyclosporine A, as described in further detail below) in order to avoid organ rejection. Once the T cell depleted immature hematopoietic cells are transplanted and chimerism is achieved, the general immune suppression agents may be tapered down and subsequently stopped. In contrast in situations in which the cell or tissue graft (e.g. solid organ) is transplanted subsequent to the T cell depleted immature hematopoietic cells, after chimerism induction, the use of general immune suppression may not required.

Ample guidance for selecting and administering suitable immunosuppressive regimens for transplantation is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Thus, according to an embodiment of the present invention, the subject is conditioned under reduced intensity conditioning prior to transplantation of a cell or tissue graft.

According to an embodiment, the reduced intensity conditioning is effected for up to 2 weeks (e.g. 1-10 or 1-7 days) prior to transplantation of the cell or tissue graft.

Thus, for example, the subject may be treated with a myeloablative or non-myeloablative conditioning. Such conditioning may comprise, for example and as described in detail in the Examples section which follows, in-vivo T cell debulking e.g. by anti-CD4 antibody, anti-CD8 antibody, anti-CD3 (OKT3®) antibodies, anti-CD52 antibodies (e.g. CAMPATH®) and/or anti-thymocyte globulin (ATG) antibody (e.g. 6 days prior to transplantation at a therapeutic effective dose of about 300 μg each).

The conditioning may additionally or alternatively comprise total body irradiation (TBI), total lymphoid irradiation (TLI, i.e. exposure of all lymph nodes, the thymus, and spleen), a chemotherapeutic agent and/or an antibody immunotherapy.

Thus, according to one embodiment, the TBI comprises a single or fractionated irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy or 10-15 Gy.

According to a specific embodiment, the TBI comprises a single or fractionated irradiation dose within the range of 1-3.5 Gy.

According to an embodiment, TBI treatment is administered to the subject 1-10 days (e.g. 1-3 days) prior to transplantation. According to one embodiment, the subject is conditioned once with TBI 1 or 2 days prior to transplantation.

According to a specific embodiment, the TLI comprises an irradiation dose within the range of 0.5-1 Gy, 0.5-1.5 Gy, 0.5-2.5 Gy, 0.5-5 Gy, 0.5-7.5 Gy, 0.5-10 Gy, 0.5-15 Gy, 1-1.5 Gy, 1-2 Gy, 1-2.5 Gy, 1-3 Gy, 1-3.5 Gy, 1-4 Gy, 1-4.5 Gy, 1-1.5 Gy, 1-7.5 Gy, 1-10 Gy, 2-3 Gy, 2-4 Gy, 2-5 Gy, 2-6 Gy, 2-7 Gy, 2-8 Gy, 2-9 Gy, 2-10 Gy, 3-4 Gy, 3-5 Gy, 3-6 Gy, 3-7 Gy, 3-8 Gy, 3-9 Gy, 3-10 Gy, 4-5 Gy, 4-6 Gy, 4-7 Gy, 4-8 Gy, 4-9 Gy, 4-10 Gy, 5-6 Gy, 5-7 Gy, 5-8 Gy, 5-9 Gy, 5-10 Gy, 6-7 Gy, 6-8 Gy, 6-9 Gy, 6-10 Gy, 7-8 Gy, 7-9 Gy, 7-10 Gy, 8-9 Gy, 8-10 Gy, 10-12 Gy, 10-15 Gy, 10-20 Gy, 10-30 Gy, 10-40 Gy, 10-50 Gy, 0.5-20 Gy, 0.5-30 Gy, 0.5-40 Gy or 0.5-50 Gy.

According to a specific embodiment, the TLI comprises a single or fractionated irradiation dose within the range of 1-3.5 Gy.

According to an embodiment, TLI treatment is administered to the subject 1-10 days (e.g. 1-3 days) prior to transplantation. According to one embodiment, the subject is conditioned once with TLI 2-7 days prior to transplantation.

According to one embodiment, the conditioning comprises a chemotherapeutic agent. Exemplary chemotherapeutic agents include, but are not limited to, Busulfan (Myleran®, Busulfex®), Fludarabine, Melphalan and Thiotepa and cyclophosphamide. The chemotherapeutic agent/s may be administered to the subject in a single dose or in several doses e.g. 2, 3, 4, 5, 6, 7, 8, 9, 10 or more doses (e.g. daily doses) prior to transplantation. According to one embodiment, the subject is administered a chemotherapeutic agent (e.g. Fludarabine e.g. at a dose of about 30 mg/m$^2$/day) for 5 consecutive days prior to transplantation (e.g. on days −7 to −3).

According to one embodiment, the conditioning comprises an antibody immunotherapy. Exemplary antibodies include, but are not limited to, an anti-CD52 antibody (e.g. Alemtuzumab sold under the brand names of e.g. Campath®, MabCampath®, Campath-1H® and Lemtrada®) and an anti-thymocyte globulin (ATG) agent [e.g. Thymoglobulin® (rabbit ATG, rATG, available from Genzyme) and Atgam® (equine ATG, eATG, available from Pfizer)]. Additional antibody immunotherapy may comprise anti-CD3 (OKT3®), anti-CD4 or anti-CD8 agents. According to one embodiment, the antibody is administered to the subject in a single dose or in several doses e.g. 2, 3, 4, 5, 6, 7, 8, 9, 10 or more doses (e.g. daily doses) prior to transplantation (e.g. 6 days prior to transplantation).

According to one embodiment, the subject is not treated chronically (e.g. for a prolonged period of time, e.g. for more than 10 days) with GVHD prophylaxis post transplant.

According to one embodiment, in case of relapse after hematopoietic stem cell transplantation, the subject may be further treated by donor lymphocyte infusions (DLIs). For example, the subject may be administered with graded doses of T-cells as previously described by Dazzi et al [Dazzi, Szydlo et al., Blood, (2000) 96: 2712-6] fully incorporated herein by reference.

According to one embodiment, the subject may be treated by infusion of about 0.5-5×10$^4$ CD3$^+$ lymphocytes per kg recipient body weight (e.g. 1×10$^4$ CD3$^+$ lymphocytes, e.g. unmanipulated CD3$^+$ lymphocytes, per kg recipient body weight) for the treatment of relapse following T cell depleted haploidentical transplantation.

According to one embodiment, a patient with early molecular and/or hematological relapse will further be treated with a first dose of about 1×10$^4$ CD3$^+$ cells per Kg recipient body weight. In the absence of GVHD, the second infusion of about $1\times10^5$ CD3$^+$ cells per kg recipient body weight will typically be given about 45 days later followed 2 months later by a third dose of about $1\times10^6$ CD3$^+$ cells per kg recipient body weight. It will be appreciated that donors typically undergo a leukoapheresis to collect lymphocytes prior to mobilization of hematopoietic cells (e.g. for transplantation). The frozen products are thawed as needed and infused quickly over a period of 5-10 minutes. Patients exhibiting acute GVHD or who fail to demonstrate hematological engraftment typically will not receive any DLI.

According to one embodiment, a patient with relapsing B cell non-Hodgkin lymphoma will typically be further treated with rituximab (e.g. 375 mg/m$^2$ weekly for about 4 weeks) with DLI concomitant with the second rituximab dose.

According to one embodiment, a patient with relapsing multiple myeloma will be further treated with bortezomib (e.g. 1.3 mg/sqm on days 1, 4, 8 and 11) before starting DLI.

According to one embodiment, no post-DLI immunosuppressive agents will be used along with the present methods.

According to an aspect of the present invention, there is provided a method of treating a subject in need of a T cell depleted immature hematopoietic cell transplantation, the method comprising: (a) transplanting into a conditioned subject a dose of T cell depleted immature hematopoietic cells, wherein the T cell depleted immature hematopoietic cells comprise less than $5\times10^5$ CD3$^+$ cells per kilogram body weight of the subject, and wherein the dose comprises at least about $5\times10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

According to an aspect of the present invention, there is provided a method of treating a subject in need of an immature hematopoietic cell transplantation, the method comprising: (a) conditioning a subject under a reduced intensity conditioning protocol, wherein the reduced intensity conditioning comprises a total body irradiation (TBI) and a chemotherapeutic agent; (b) transplanting into the subject a dose of T cell depleted immature hematopoietic cells, wherein the T cell depleted immature hematopoietic cells comprise less than $5\times10^5$ CD3+ cells per kilogram body weight of the subject, and wherein the dose comprises at least about $5\times10^6$ CD34+ cells per kilogram body weight of the subject; and subsequently (c) administering to the subject a therapeutically effective amount of cyclophosphamide, wherein the therapeutically effective amount comprises 25-200 mg per kilogram body weight, thereby treating the subject.

According to an aspect of the present invention, there is provided a method of inducing donor specific tolerance in a subject in need of a non-syngeneic cell or tissue graft, the method comprising: (a) transplanting into a subject a dose of T cell depleted immature hematopoietic cells obtained from a non-syngeneic donor, wherein the T cell depleted immature hematopoietic cells comprise less than $5\times10^5$ CD3$^+$ cells per kilogram body weight of the subject, and wherein the dose comprises at least about $5\times10^6$ CD34+ cells per kilogram body weight of the subject; and subsequently (b) administering to the subject a therapeutically effective amount of cyclophosphamide, wherein the therapeutically effective amount comprises 25-200 mg per kilogram body weight, thereby treating the subject.

As used herein, the term "donor specific tolerance" as used herein refers to a condition in which there is a decreased responsiveness of the recipient's cells (e.g. recipient's T cells) when they come in contact with the donor's cells (e.g. donor hematopoietic cells) as compared to the responsiveness of the recipient's cells in the absence of such a treatment method.

Tolerance induction enables transplantation of a cell or tissue graft (as described in further detail hereinabove) with reduced risk of graft rejection or GVHD.

According to one embodiment of the present invention, patients with early molecular and/or hematological relapse may receive donor lymphocyte infusions (DLI).

According to one embodiment of the present invention, DLI may comprise $1\times10^3$-$1\times10^6$ CD3$^+$ T cell/Kg recipient body weight.

According to one embodiment, patients with early molecular and/or hematological relapse may receive a single dose or several doses (two, three, four, five or more doses) of DLI.

Thus, for example, patients with early molecular and/or hematological relapse may receive a first dose of $1\times10^4$ CD3$^+$ T cell/Kg recipient body weight. In the absence of graft versus host disease (GVHD), a second infusion of $1\times10^5$ CD3$^+$ T cell/kg recipient body weight may be given e.g. 45 days later followed e.g. 2 months later by a third dose of $1\times10^6$ CD3$^+$ T cell/kg recipient body weight.

According to one embodiment, patients with early molecular and/or hematological relapse may receive total body irradiation (TBI), total lymphoid irradiation (TLI), a chemotherapeutic agent and/or an antibody immunotherapy.

Thus, for example, patients with relapsing B cell non-Hodgkin lymphoma may receive rituximab (e.g. at a dose of 375 mg/m$^2$ weekly) for about 4 weeks with DLI concomitant with the second rituximab dose.

Thus, for example, patients with relapsing multiple myeloma may be treated with bortezomib (e.g. at a dose of 1.3 mg/sqm on days 1, 4, 8 and 11) before starting DLI.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Stable Engraftment of HLA Mismatched Bone Marrow Following Transplantation of 'Mega Dose' Bone Marrow and Post Transplantation Cyclophosphamide Materials and Experimental Procedures Animals Mice used in these studies were 6-12 week old female mice. Balb/c-Nude (H-2d) and C3H/Hen (H-2k) were purchased from Harlan Israel (Rehovot, Israel). All mice were kept in small cages (5 animals in each cage) and fed sterile food and acid water. These studies were approved by the Weizmann Institute of Science, Institutional Animal Care and Use Committee.

Transplantation Protocol

Low ($5 \times 10^6$) and high dose ($25 \times 10^6$) Balb/c-Nude BM cells (providing a source of BM depleted of T cells) were transplanted into allogeneic recipients (C3H/Hen) on day 0 following in-vivo T cell debulking (TCD) with anti-CD4 (clone GK1.5) and anti-CD8 (clone 53.6.72) antibodies (300 µg each; Bio X Cell, NH, USA) delivered on day −6, and exposure to 2.0 Gy total body irradiation (TBI) on day −1. High dose Cyclophosphamide (CY, 100 mg/kg, Baxter Oncology, Germany) was administered on days +3 and +4 post transplant and donor type chimerism was evaluated 35 and 95 days post transplant using fluorescein anti-host and donor H-2 antibodies (e.g. FITC labeled anti-H-2$D^d$ antibody specific for donor type cells and PE labeled anti-H-2$K^k$ antibody specific for host type cells).

Skin Graft Protocol

Donor (Balb/c) and $3^{rd}$ party (C57BL/6) skin grafts were transplanted to the mixed chimeric recipients as described above [i.e. to those mice which were previously transplanted with mega dose ($25 \times 10^6$) T cell depleted BM and were treated with high dose CY] and to the recipient mice that were inoculated with a regular ($5 \times 10^6$) T cell depleted BM cell dose and were treated with high dose CY.

Results

To test the potential synergy between 'mega dose' T cell depleted bone marrow transplant (BMT) and high dose cyclophosphamide (CY) post transplant, after reduced intensity conditioning (RIC) of the recipient mice, the following experiments were carried out.

Recipient mice (C3H/Hen) were treated with a conditioning protocol prior to transplantation of a T cell depleted bone marrow transplant. Specifically, mice were in-vivo treated with T cell debulking (TCD) using anti-CD4 and anti-CD8 antibodies delivered on day −6 and by exposure to 2.0 Gy total body irradiation (TBI) on day −1. Next, low (5×10⁶) or high dose (25×10⁶) Balb/c-Nude BM cells (providing a source of BM depleted of T cells, as Nude mice have miniscule numbers of mature T cells) were transplanted into allogeneic recipients (C3H/Hen) on day 0. High dose cyclophosphamide (CY, 100 mg/kg) was administered on days +3 and +4 post transplant. Evaluation of bone marrow cell engraftment was evaluated by donor type chimerism at 35 and 95 days post transplant.

As shown in FIGS. 1A-1B and FIGS. 2A-2B, chimerism analysis on day 35 and day 95 revealed that none of the control mice (conditioned with TCD, 2 Gy TBI and optionally CY, but did not receive BM) expressed donor type chimerism. Similarly, none of the BM mice recipients that were transplanted with a regular dose of 5×10⁶ T cell depleted BM, in the presence or absence of cyclophosphamide treatment, expressed donor type chimerism. However when the dose of T cell depleted BM was increased to 25×10⁶ cells, durable mix chimerism was achieved in 4 out of 7 mice that were also treated with cyclophosphamide on days +3 and +4 post transplant (see FIGS. 1A-1B and FIG. 2C).

Further follow-up of these recipient mice at 180 and 225 days post transplant revealed that the chimerism induced was stable and durable (FIG. 3). As illustrated in FIG. 3, the number of donor type chimeric recipients and the level of donor chimerism remained unchanged 225 days post transplant, suggesting that tolerance has been achieved.

Tolerance induction was measured by transplantation of donor (Balb/c) and 3$^{rd}$ party (C57BL/6) skin grafts to the mixed chimeric recipients that were transplanted with mega dose (25×10⁶) T cell depleted BM and were treated with high dose CY (as described above), in comparison to the recipients that were inoculated with a regular (5×10⁶) T cell depleted BM cell dose (as described above).

As shown in FIGS. 4A-4B, three out of 4 chimeric mice that were transplanted with 25×10⁶ T cell depleted BM accepted the donor graft and rejected the 3$^{rd}$ party skin grafts. In contrast, recipient mice that were inoculated with 5×10⁶ T cell depleted BM cells and CY rejected both the donor and 3$^{rd}$ party skin grafts (FIG. 4A).

These results illustrate that the combination of mega dose T cell depleted BM and high dose Cyclophosphamide treatment allows the successful engraftment of hematopoietic stem cells, under reduced intensity conditioning, along with tolerance induction.

Encouraged by these results a set of calibration experiments were initiated in order to determine the optimal irradiation and Cyclophosphamide dose to improve chimerism induction by this approach.

Example 2

The Effect of Different Doses of Total Body Irradiation (TBI) on Chimerism

Materials and Experimental Procedures
Animals
As described in Example 1, hereinabove.
Transplantation Protocol
High dose (25×10⁶) Balb/c-Nude BM cells (providing a source of BM depleted of T cells) were transplanted into allogeneic recipients (C3H/Hen) on day 0 following in-vivo T cell debulking (TCD) with anti-CD4 (clone GK1.5) and anti-CD8 (clone 53.6.72) antibodies (300 μg each; Bio X Cell, NH, USA) delivered on day −6, and exposure to different doses of irradiation ranging from 1 to 3.5 Gy TBI on day −1. High dose Cyclophosphamide (CY, 100 mg/kg, Baxter Oncology, Germany) was administered on days +3 and +4 post transplant and donor type chimerism was evaluated 30 days post transplant using fluorescein anti-host and donor H-2 antibodies (e.g. FITC labeled anti-H-2D$^d$ antibody specific for donor type cells and PE labeled anti-H-2K$^k$ antibody specific for host type cells).

Results

In this experiment, the minimal irradiation dose was defined. 'Mega dose' (25×10⁶) Balb/c-Nude T cell depleted BM was transplanted into 5 groups of allogeneic recipients (C3H/Hen) on day 0 following T cell debulking (with anti-CD4 and anti-CD8 antibodies) on day −6, and different doses of irradiation (ranging from 1 to 3.5 Gy TBI) on day −1. High dose Cyclophosphamide (CY) was administered on days +3 and +4 post transplant and donor type chimerism was evaluated at 30 days post transplant.

As can be seen in FIG. 5, all the recipient mice that were irradiated with 2.5, 3 or 3.5 Gy TBI (6/6) were chimeric, exhibiting donor type chimerism ranging between 58-83%. Similarly, 87% (13/15) of the mice treated with 2 Gy TBI exhibited donor type chimerism ranging between 56-85%.

Further reduction of the irradiation dose to 1.0 Gy caused a small reduction in the percentage of chimeric mice, namely 83% (5/6), however the donor type chimerism range was significantly reduced to 14.5-58%.

Example 3

The Effect of Different Cyclophosphamide (CY) Doses on Chimerism

Materials and Experimental Procedures
Animals
As described in Example 1, hereinabove.
Transplantation Protocol
High dose (25×10⁶) Balb/c-Nude BM cells (providing a source of BM depleted of T cells) were transplanted into allogeneic recipients (C3H/Hen) on day 0 following in-vivo T cell debulking (TCD) with anti-CD4 (clone GK1.5) and anti-CD8 (clone 53.6.72) antibodies (300 μg each; Bio X Cell, NH, USA) delivered on day −6, and exposure to 2.0 Gy total body irradiation (TBI) on day −1. Different doses of Cyclophosphamide (CY, 100 mg/kg, 125 mg/kg or 150 mg/kg, Baxter Oncology, Germany) were administered on days +3 and +4 post transplant and donor type chimerism was evaluated 30 days post transplant using fluorescein anti-host and donor H-2 antibodies (e.g. FITC labeled anti-H-2D$^d$ antibody specific for donor type cells and PE labeled anti-H-2K$^k$ antibody specific for host type cells).

Results

In this experiment, the optimal dose of CY post transplant was defined. 'Mega dose' (25×10⁶) Balb/c-Nude BM cells were transplanted into 3 groups of allogeneic recipients (C3H/Hen) on day 0 following T cell debulking (TCD) with anti-CD4 and anti-CD8 antibodies on day −6, and 2 Gy TBI on day −1. Different doses of Cyclophosphamide (CY), 100 mg/kg, 125 mg/kg or 150 mg/kg, were administered on days +3 and +4 post transplant and donor type chimerism was performed 30 days post transplant.

As can be seen in FIG. 6, increasing CY dose to 125 mg/kg or 150 mg/kg did not provide a significant enhancement of chimerism. Thus, the recipient mice that were treated with 100 mg/kg, 125 mg/kg or 150 mg/kg CY exhibited an average of 57.5±25.8, 66.5±20.6 or 67.4±27.4 donor type chimerism, respectively. No statistical significance was found when the recipients treated with 100 mg/kg were compared to those treated with 125 mg/kg or 150 mg/kg (P=0.5 and p=0.469 respectively).

Example 4

CD8+ Non-T Cells are not Important for Attaining Chimerism by Combining 'Mega Dose' T Cell Depleted BM with CY Post Transplant Materials and Experimental Procedures
Animals
As described in Example 1, hereinabove.
Transplantation Protocol High dose (25×10$^6$) of CD8 depleted and non-depleted Balb/c-Nude BM cells were transplanted into 2 cohorts of allogeneic recipients (C3H/Hen) on day 0 following in-vivo T cell debulking (TCD) with anti-CD4 (clone GK1.5) and anti-CD8 (clone 53.6.72) antibodies (300 μg each; Bio X Cell, NH, USA) delivered on day −6, and exposure to 2.0 Gy total body irradiation (TBI) on day −1. High dose Cyclophosphamide (CY, 100 mg/kg, Baxter Oncology, Germany) was administered on days +3 and +4 post transplant and donor type chimerism was evaluated 30 days post transplant using fluorescein anti-host and donor H-2 antibodies (e.g. FITC labeled anti-H-2D$^d$ antibody specific for donor type cells and PE labeled anti-H-2K$^k$ antibody specific for host type cells).

The BM source in these experiments was Balb/c-Nude mice. Moreover, the transplanted mice in these experiments were athymic and as such they lacked T cells.

However in order to refute the possibility that the effect was a contribution of residual non-T CD8 cells, the BM preparation from Balb/c-Nude mice was negatively sorted for CD8 cells using a cell sorting system (e.g. anti-CD8 magnetic beads or FACS sorter).

Results

As Ildstad et al. previously taught that a subset of CD8+ TCR− BM cells are critical for achieving donor type chimerism [Fugier-Vivier I J et al., *J Exp Med* (2005) 201:373-383; Grimes H L et al., *Exp Hematol.* (2004) 32:946-954; Huang Y et al., *Blood* (2011) 117:2494-2505; Kaufman C L et al., *Blood* (1994) 84:2436-2446; Leventhal J et al., *BMC Med* (2012) 10:48; Leventhal J et al., *Sci Transl Med.* (2012) 4:124ra128], the present inventors depleted residual CD8+ cells from the Balb/c-Nude 'mega dose' BM preparation, and measured chimerism induction compared to control non-CD8+ depleted Nude BM cells.

As can be seen in FIG. 7, depletion of CD8+ T cells from the BM preparation did not have any adverse impact on the level of chimerism achieved when combing 'mega dose' T cell depleted BM cells with post transplant CY.

Example 5

Clinical Protocol

Study Design

This is a prospective, observational, phase I/II multicenter study. Ten patients with hematological disorders will be enrolled over a one year period.

The primary endpoint of the study is engraftment and 10 evaluable patients (i.e. patients surviving beyond day 28) will be entered. An acceptable primary graft failure or rejection rate is approximately 10%.

Study Duration

The primary analysis will be conducted using 6 and 12 months follow-up data. Patients will be followed-up until 48 months after transplantation.

Definitions

Stable sustained engraftment is defined as neutrophils, more than 1000/μl for three consecutive days, and platelets, more than 20000/μl for three consecutive days, without transfusion.

Graft rejection is defined as rapid decline of neutrophils, less than 100/μl after documented neutrophil engraftment, with or without increase of lymphocytes.

Graft failure is defined as failure to reach more than 1000/μl neutrophils for three consecutive days and more than 20000/μl platelets for three consecutive days without transfusion at day +28.

The secondary endpoint of the study is the incidence of grade II-IV acute GVHD. An acceptable incidence of grade II-IV acute GVHD is approximately 10%.

For acute GVHD grading criteria is indicated in Tables 1A-B, below.

TABLE 1A

Clinical staging of acute GVHD

| Stage | SKIN | LIVER | GUT |
|---|---|---|---|
| + | Rash more than 25% | Bilirubin = 2-3 mg/dl | Diarrhea 500-1000 ml |
| ++ | Rash 25-50% | Bilirubin = 3-6 mg/dl | Diarrhea 1000-1500 ml |
| +++ | Generalized erythroderma | Bilirubin = 6-15 mg/dl | Diarrhea more than 1500 ml |
| ++++ | Desquamation and bullae | Bilirubin more than 15 mg/dl | Pain or ileus |

TABLE 1B

Clinical grading of acute GVHD

| GRADE | SKIN | LIVER | GUT | Functional impairment |
|---|---|---|---|---|
| 0 none | 0 | 0 | 0 | 0 |
| I mild | + to ++ | 0 | 0 | 0 |
| II moderate | + to +++ | + | + | + |
| III severe | ++ to +++ | ++ to +++ | ++ to +++ | ++ |
| IV/life threatening | ++ to ++++ | ++ to ++++ | ++ to ++++ | +++ |

Statistical Considerations

The time intervals for engraftment, survival, disease-free survival, relapse rate and risk of transplant-related mortality will be calculated from the day of stem cell transplantation. Actuarial curves will be calculated according to the Kaplan-Meier method.

Eligibility Criteria

Inclusion Criteria—Patient

Age—more or equal to 18 and less or equal to 70 years old

CLL patients with refractoriness to fludarabine or other chemotherapy due to the p53 loss by 17p deletion and/or TP53 mutation Follicular lymphoma with either unfavorable cytogenetics such as complex karyotype, del17p, del 6q23-26, mutations in TP53, minus 1p Hodgkin's Lymphoma relapsed after autologous transplantation, not eligible for immunotherapy with anti-CD30

Multiple myeloma relapsing after autologous transplantation, with unfavorable cytogenetics in either partial or complete remission Severe Aplastic Anemia relapsing after immunotherapy Absence of fully HLA-matched or one locus HLA-mismatched family donor Absence of matched unrelated donor or ineligibility for donor search in the donor registry (IBMDR)

Presence of haploidentical family donor and a back-up of patient autologous stem cells Stable clinical conditions and life expectancy of more than 12 weeks Karnofsky—more than 70%

Written informed consent

Pre-Treatment Evaluation complete clinical history and examination and determination of performance status and body surface area.

complete blood count blood group, red blood cells subgroups, anti-A and/or anti-B agglutinin titration creatinine clearance, uric acid, ferritin, LDH, beta 2 microglobulin, protein electrophoresis, SGOT, SGPT, urine test, blood glucose, blood nitrogen, immunoglobulin levels, Coombs tests.

pregnancy test

HIV-ab, HBsAg, HBVDNA, HCV-ab, HCVRNA, CMV-ab, Toxoplasma-ab, HSVab

ECG and measurement of ejection fraction by ultrasound or scintigraphic test.

chest X ray.

lung CT scan, brain CT scan, maxillary sinus CT scan.

dental X ray and examination.

biopsy and bone marrow aspirate for morphologic and cytogenetic analysis, search for a molecular marker (if not known) and FACS analysis (according to underlying disease).

neurologic examination and lumbar puncture in patient at risk.

radiologic scan (CT, NMR) of the known disease localization.

complete serologic and molecular HLA typing, ML cultures and cytotoxicity test with the selected donors.

cytotoxic anti HLA antibodies.

Abdominal echography

Exclusion Criteria—Patient

History of central nervous system disease localization

Positivity for HIV, HCV, HCVRNA, HBsAg, HBVDNA

Active and documented pneumonia of any kind, fungal tissue infection, viral positive cultures of respiratory secretion or blood bilirubin of more than 2 times normal blood creatinine clearance less than 50 ml/min DLCO less than 50% of the predicted value ejection fraction less than 45% (or myocardial stroke in the last year)

pregnancy or lactation psychiatric disorders

Eligibility Criteria—Donor

Absence of hematopoietic or marrow function related disease that interferes with the collection of sufficient numbers of normal progenitor cells.

Absence of any medical condition that would pose a serious health risk by undergoing peripheral blood stem cell harvest Negative HIV, HTLV-1 tests Any healthy family member will be considered for hematopoietic stem cell donation. Selection of a donor will be based on typing of HLA-A, B, C, DR loci to be carried out on the recipient, siblings, parents and possibly other family members such as aunts, uncles and cousins. A prospective related donor must be at least genotypically HLA-A, B, C, DR haploidentical to the patient, but can differ for 2-3 HLA alleles on the unshared haplotype.

Donor will be selected preferentially on the basis of the donor-versus-recipient NK alloreactivity.

Donor Evaluation

Complete history, physical examination and examination of physical veins by the pheresis service for determination of suitability for pheresis via peripheral veins.

Blood tests: WBC, PLT, Hb, PT, PTT, total protein, albumin, electrolytes, glucose, SGOT/SGPT, alkaline phosphatase, bilirubin, LDH, acid uric, creatinine.

CMV, EBV, HSV, VZV, Hepatitis B+C, HIV, Toxoplasma serology.

Complete red blood cell typing

Serology for Syphilis, CMV, EBV, HSV, VZV, Hepatitis B+C, HTLV-1, HIV, Toxoplasmosis.

Transfusion transmitted disease testing must be performed between 30 and 7 days prior to stem cell collection Chest X-ray

EKG

VNTR analysis by PCR

Donors will be prioritized on the basis of younger age, better health, and being CMV-negative for CMV-negative recipients.

Exclusion Criteria—Donor

A positive HIV or HTLV-1 test or evidence of active/persistent viral hepatitis infection will exclude the donor from participation in this study.

Presence of any medical condition that would pose a serious health risk by undergoing peripheral blood stem cell harvest (i.e. insulin-dependent diabetes, cardiovascular disorders, chronic inflammatory diseases).

Treatment Procedures

Mobilization of Donor HSC and Graft Processing.

Patients are required to have a family donor (aged 18 to 60 yrs), willing and capable of donating filgrastim/lenogastrim-stimulated peripheral blood hematopoietic cells. Donors will be screened according to Blood Bank general rules. It is advisable to perform an exercise EKG testing in donors above 50 yrs of age. Normal donors will receive filgrastim or lenogastrim 5 mcg/kg subcutaneously every 12 hours; on day 5 the leukapheresis will be started. Filgrastim/Lenogastrim dosage will be adjusted to maintain white blood cells below $60 \times 10^9$/L. On the $4^{th}$ day of filgrastim/lenogastrim treatment, if the circulating CD34+ cell count is more than 40/µL, the donor will start leukapheresis. Daily leukapheresis will be continued for a planned 3 days, with a maximum of 4 days, to collect a target cell dose of more than $10 \times 10^6$ CD34+ cells/kg.

If the target is reached early, collection can continue for 3 total days in order to give the largest possible dose. If the donor does not tolerate the procedure in any of its component parts, an alternative donor may be used if available. If a site is unable to collect more than $10 \times 10^6$ CD34+ cells/kg from an appropriate donor, patients may not proceed on study. PBPCs will be depleted of donor T and B cells by selection of CD3+ and/or CD19+ cells using a cell sorting system (e.g. anti-CD3/19 magnetic beads or FACS sorter).

Target value of CD34-positive cells will be at least $10 \times 10^6$/kg of the recipient body weight (b.w.).

The apheresis will be performed through the antecubital veins.

TABLE 2

| Conditioning regimen | |
|---|---|
| day −7 | Fludarabine 30 mg/sqm |
| day −6 | Fludarabine 30 mg/sqm |
| day −5 | Fludarabine 30 mg/sqm |
| day −4 | Fludarabine 30 mg/sqm |
| day −3 | Fludarabine 30 mg/sqm |
| day −2 | TBI 2 Gy single fraction |
| day −1 | Rest |
| day 0 | Graft |
| day +1 | Rest |
| day +2 | Rest |
| day +3 | CY 50 mg/kg |
| day +4 | CY 50 mg/kg |

As described in Table 2, above, fludarabine will be administered intravenously daily on 5 sequential days, −7, −6, −5, −4, and −3, at a dose of 30 mg/m². Each dose will be infused over 30 minutes. TBI 200 cGy will be given on day −1 in a single fraction.

On day 0, $CD3^-/CD19^-$ immunoselected HSCs will be thawed, washed and infused through a central access.

CY will be administered intravenously in one hour on days +3 and +4 post-transplantation at 50 mg/kg/day.

Special Management Orders a. a double-lumen central venous line will be placed before conditioning regimen;

b. for urate prophylaxis allopurinol 300 mg per os will be given;

c. antiemetic therapy will be given according to single center guidelines;

d. transfusion of filtered and irradiated blood products. Keep hemoglobin level more than 8 g/L and platelets more than 15000/μL in absence of fever or bleeding signs;

Patient Monitoring During Treatment a. daily full blood count and differential b. serum creatinine, Na+, K+, Ca++, bilirubin daily during chemotherapy and hyper-hydration c. liver function tests, albumin, coagulation tests with antitrombin III, cytomegalovirus antigenemia and PCR twice a week.

d. surveillance cultures according to center guidelines

Toxicity Evaluation

Toxicity will be evaluated according to WHO criteria, as indicated in Table 3, below.

TABLE 3

| WHO toxicity criteria | | | | | |
|---|---|---|---|---|---|
| | Grade 0 | Grade 1 | Grade 2 | Grade 3 | Grade 4 |
| Hematological | | | | | |
| Hemoglobin | >11.0 g/dl 6.8 mmol/l | 9.5-10.9 g/dl 5.6-6.7 mmol/l | 8.0-9.4 g/dl 4.9-5.6 mmol/l | 6.5-7.9 g/dl 4.0-4.9 mmol/l | <6.5 g/dl <4.0 mmol/l |
| Leukocytes (1000/mm) | ≥4.0 | 3.0-3.9 | 2.0-2.9 | 1.0-1.9 | <1.0 |
| Granulocytes (1000/mm) | ≥2.0 | 1.5-1.9 | 1.0-1.4 | 0.5-0.9 | <0.5 |
| Platelets (1000/mm) | ≥100 | 75-99 | 50-74 | 25-49 | <25 |
| Hemorrhage | None | Petechiae | Mild blood loss | Gross blood loss | Debilitating blood loss |
| Gastrointestinal | | | | | |
| Bilirubin | ≤1.25 × N* | 1.26-2.5 × N* | 2.6-5 × N* | 5.1-10 × N* | >10 × N* |
| Transaminases (SGOT SGPT) | ≤1.25 × N* | 1.26-2.5 × N* | 2.6-5 × N* | 5.1-10 × N* | >10 × N* |
| Alkaline phosphotase | ≤1.25 × N* | 1.26-2.5 × N* | 2.6-5 × N* | 5.1-10 × N* | >10 × N* |
| Oral | No change | Soreness/erythema | Erythema, ulcers: can eat solids | Ulcers: requires liquid diet only | Alimentation not possible |
| Nausea/vomiting | None | Nausea | Transient vomiting | Vomiting requiring therapy | Intractable vomiting |
| Diarrhoea | None | Transient < 2 days | Tolerable, but >2 days | Intolerable, requiring therapy | Hemorrhagic dehydration |
| Renal | | | | | |
| Blood urea or creatinine | ≤1.25 × N* | 1.26-2.5 × N* | 2.6-5 × N* | 5-10 × N* | >10 × N* |
| Proteinuria | No change | 1+ <0.3 g % <3 g/l | 2-3+ 0.3-1.0 g % 3-10 g/l | 4+ >1.0 g % >10 g/l | Nephrotic syndrome |
| Hematuria | No change | Microscopic | Gross | Gross + clots | Obstructive uropathy |
| Pulmonary | No change | Mild symptoms | Exertional dyspnoea | Dyspnoea at rest | Complete bed rest required |
| Fever with drug | None | Fever <38° C. | Fever 38-40° C. | Fever >40° C. | Fever with hypotension |

TABLE 3-continued

WHO toxicity criteria

|  | Grade 0 | Grade 1 | Grade 2 | Grade 3 | Grade 4 |
|---|---|---|---|---|---|
| Allergic | No change | Oedema | Bronchospasm: no parenteral therapy needed | Bronchospasm: parenteral therapy required | Anaphylaxis |
| Cutaneous | No change | Erythema | Dry desquamation, vesiculation, pruritus | Most desquamation, ulceration | Exfoliative dermatitis: necrosis requiring surgical intervention |
| Hair | No change | Minimal hair loss | Moderate, patchy alopecia | Complete alopecia but reversible | Non-reversible alopecia |
| Infection (specify site) | None | Minor infection | Moderate infection | Major infection | Major infection with hypotension |
| Cardiac |  |  |  |  |  |
| Rhythm | No change | Sinus tachycardia, >110 at rest | Unifocal PVC atrial arrhythmia | Multifocal PVC | Ventricular tachycardia |
| Function | No change | Asymptomatic, but abnormal cardiac sign | Transient symptomatic dysfunction: no therapy required | Symptomatic dysfunction responsive to therapy | Symptomatic dysfunction non-responsive to therapy |
| Pericarditis | No change | Asymptomatic effusion | Symptomatic: no tap required | Tamponade: tap required | Tamponade: surgery required |
| Neurotoxicity |  |  |  |  |  |
| State of consciousness | Alert | Transient therapy | Somnolence < 50% of waking hours | Somnolence > 50% of waking hours | Coma |
| Peripheral | None | Paresthesias and or decreased tendon reflexes | Severe paresthesias and or mild weakness | Intolerable paresthesias and or marked motor loss | Paralysis |
| Constipation** | None | Mild | Moderate | Abdominal distension | Distension and vomiting |
| Pain | None | Mild | Moderate | Severe | Intractable |

N* upper limit of normal value of population under study.
**This does not include constipation resultant from narcotics
+Only treatment-related pain is considered, not disease-related pain.
Use of narcotics may be helpful in grading pain depending on the patient's tolerance.

Supportive Care

Monitoring and Treatment of Bacterial and Fungal Infections

Patients are cared for in isolation rooms with laminar airflow or high-efficiency air-particulate filtration. Liposomal Amphotericin is given at 1 mg/kg/day from day −5 to engraftment as antifungal prophylaxis. Bacterial infections are monitored by swabs and blood cultures weekly. Intravenous antibiotic therapy is started on the basis of clinical signs of infection (fever of unknown origin) or positive blood cultures. If the patient is still febrile after 72 hours, empiric antifungal therapy is started using either L-AMB 3 mg/kg/day or Voriconazole 8 mg/kg/day i.v. Vancomycin is added after an additional 72 hours of fever, or in the presence of Gram+ sepsis, or positive blood culture.

Prophylaxis, Monitoring and Treatment of Cytomegalovirus Infections

In recipients who are seropositive for CMV antibody, CMV prophylaxis consists of ganciclovir (10 mg/kg/day) between the tenth and second day before stem cell infusion. Ganciclovir is reintroduced as preemptive therapy from day +21 until day +360. CMV antigenemia/PCR is determined weekly in blood samples. If CMV antigenemia/PCR develops, patients will be treated with ganciclovir (10 mg/kg/day) or foscarnet (180 mg/kg/day).

The blood products are irradiated (30 Gy) before transfusion.

Post-Transplant Laboratory Evaluation:

1. Daily complete hemograms until granulocytes and platelets are self-sustaining, then three times/week until discharge; at least every week post discharge to day 100 and then every 2 weeks to 12 months.

2. Screening profile with liver and renal function tests twice weekly for the first 30 days, then weekly to discharge; more frequently if clinically indicated.

3. Bone marrow aspirates for morphology analysis of chimerism by FISH (sex-mismatched grafts) or cytogenetics will be done at approximately 1, 3, 6, 12 months, and every 4 months thereafter for approximately 3 years. Additional analysis will be done as clinically indicated. Patients with CML will be also monitored for bcr/abl evidence of recurrence.

4. Immunological reconstitution will be monitored by in vitro assays, including phenotypic analysis of circulating lymphocytes, assessment of natural killer and lymphokine activated killer cell function, lymphocyte transformation responses to T-cell and B-cell mitogens and immunoglobulin levels.

Follow-Up

Until day +90 complete blood counts, antigenemia and PCR for CMV, reactive protein C, complete liver and renal function will be assess twice a week.

Every two weeks until +90 peripheral blood phenotype (CD3, CD4, CD8, CD19, CD56, CD57, HLADR), chest Xray.

Every two weeks from +90 till +180:

complete blood counts, antigenemia and PCR for CMV, reactive protein C, complete liver and renal function.

Monthly:

immunoglobulin levels, protein electrophoresis, after +90 peripheral blood phenotype (CD3, CD4, CD8, CD19, CD56, CD57, HLADR), chest Xray.

after +180 complete blood counts, antigenemia and PCR for CMV, reactive protein C, complete liver and renal function.

Complete restaging of disease will be performed 2, 4, 6, 8, 12, 18 and 24 months after transplantation then annually, this will include assessment of donor chimerism by PCR analysis of HLA on peripheral blood and bone marrow cells.

For Performance Status grading criteria see Table 4, below.

TABLE 4

Karnofsky Performance scale

| FUNCTIONAL STATUS | RATING | GROUP SCORES |
|---|---|---|
| Normal. No complaints. No evidence of disease. | 100 | Rehabilitated (80+) |
| Able to carry on normal activity. Minor signs or symptoms of disease. | 90 | |
| Normal activity with effort. Some signs or symptoms of disease. | 80 | |
| Cares for self. Unable to carry on normal activity or do active work. | 70 | Self-care only (70-90) |
| Requires occasional assistance, but able to care for most needs. | 60 | Requires Caretaker (40-69) |
| Requires considerable assistance and frequent medicalc are. | 50 | |
| Disabled. Requires special care and assistance. | 40 | |
| Severely disabled. Hospitalisation is indicated, although death is not imminent. | 30 | Requires institutionalisation (1-39) |
| Very sick. Hospitalisation necessary. | 20 | |
| Moribund. Fatal processes progressing. | 10 | |
| Dead. | 0 | |

Programmed Infusions of Donor Lymphocytes

Donor lymphocyte infusions (DLIs) are effective to treat relapses after allogeneic HSCT. Nevertheless, the success of DLI has been limited to some extent by the morbidity and mortality associated with GVHD. Graded doses of T-cells are less likely to produce GVHD than a single large infusion and appear to be as effective to induce remission [Dazzi, Szydlo et al., Blood, (2000) 96: 2712-6]. A recent dose finding study has shown that $1 \times 10^4$ unmanipulated CD3$^+$ lymphocyte/kg recipient b.w. can be safely infused in patients who have received a T cell depleted haploidentical transplantation [Lewalle P. et al. Bone Marrow Transplant (2002) 29 (suppl 2): S26, 0164a].

Patients with early molecular and/or hematological relapse will receive a first dose of $1 \times 10^4$ CD3$^+$ cell/Kg recipient b.w.; in the absence of GvHD, the second infusion of $1 \times 10^5$ CD3$^+$ cell/kg will be given 45 days later followed 2 months later by a third dose of $1 \times 10^6$ CD3$^+$ cell/kg. Donors will undergo a leukoapheresis to collect lymphocytes prior to mobilization of hematopoietic cells because it has been shown that G-CSF has an immune-modulatory effect on some T lymphocyte subsets, decreasing their responsiveness to allogeneic stimuli. The frozen products will be thawed and infused quickly over a period of 5-10 minutes. Patients with acute GvHD or who fail to demonstrate hematological engraftment will not receive any DLI.

Patients with relapsing B cell non-Hodgkin lymphoma will receive rituximab 375 mg/m$^2$ weekly for 4 weeks with DLI concomitant with the second rituximab dose. Patients with relapsing multiple myeloma will be treated with bortezomib (1.3 mg/sqm on days 1, 4, 8 and 11) before starting DLI.

No post-DLI immunosuppressive agents will be used.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety

What is claimed is:

1. A method of reducing graft rejection and/or graft versus host disease (GVHD) or inducing donor specific tolerance in a subject in need thereof, the method comprising:
   (a) transplanting into a subject conditioned under non-myeloablative conditioning, wherein said non-myeloablative conditioning comprises a chemotherapeutic agent, a dose of T cell depleted immature hematopoietic cells obtained from a non-syngeneic donor, wherein said dose of said T cell depleted immature hematopoietic cells comprises less than $5 \times 10^5$ CD3$^+$ cells per kilogram body weight of the subject, and wherein said dose comprises at least $5 \times 10^6$ CD34+ cells per kilogram body weight of the subject; and subsequently
   (b) administering to the subject a therapeutically effective amount of cyclophosphamide, wherein said therapeutically effective amount comprises 25-200 mg cyclophosphamide per kilogram body weight of the subject, and wherein said cyclophosphamide is administered to the subject in two doses on days 3 and 4 following step (a), and wherein said subject is not treated with GVHD prophylaxis for more than 10 days post-transplant, thereby reducing graft rejection and/or GVHD.

2. The method of claim 1, wherein the non-myeloablative conditioning further comprises in-vivo T cell debulking.

3. The method of claim 2, wherein said in-vivo T cell debulking is effected by antibodies, and optionally wherein said said antibodies comprise at least one of an anti-thymocyte globulin (ATG) antibody, an anti-CD52 antibody, and anti-CD3 antibody.

4. The method of claim 1, wherein the non-myeloablative conditioning further comprises a total body irradiation (TBI) or a total lymphoid irradiation (TLI).

5. The method of claim 1, wherein said conditioning is effected 1-10 days prior to said transplanting.

6. The method of claim 1, wherein said chemotherapeutic agent comprises at least one of Fludarabine, Busulfan, Melphalan, Thiotepa and cyclophosphamide.

7. The method of claim 1, wherein said dose of said T cell depleted immature hematopoietic cells:
(i) comprises $5\text{-}40\times10^6$ CD34+ cells per kilogram body weight of the subject; and/or
(ii) comprises less than $0.5\times10^6$ CD8$^+$ TCR$\alpha/\beta^-$ cells per kilogram body weight of the subject; and/or
(iii) comprises T cell depleted G-CSF mobilized peripheral blood progenitor cells; and/or
(iv) are obtained by T cell debulking; and/or
(v) are treated by B cell debulking.

8. The method of claim 1, wherein said amount of said cyclophosphamide is about 100-200 mg per kg body weight.

9. The method of claim 1, wherein each of said two doses of said cyclophosphamide comprises an amount of about 50 mg per kg body weight.

10. The method of claim 1, wherein the subject:
(I) is a human subject; and/or
(II) has a malignant disease and optionally wherein said malignant disease is a hematopoietic cancer; or
(III) has a non-malignant disease and optionally wherein said non-malignant disease is a genetic disease or disorder, a hematopoietic abnormality, an autoimmune disease or a metabolic disorder; or
(IV) is in need of a cell or tissue graft, and optionally:
(i) wherein cell or tissue graft is selected from the group consisting of a liver, a pancreas, a spleen, a kidney, a heart, a lung, a skin, an intestine and a lymphoid tissue or organ; and/or
(ii) wherein said cell or tissue graft is transplanted into the subject prior to, concomitantly with or following said transplanting said dose of said T cell depleted immature hematopoietic cells into said subject; and/or
(iii) wherein said cell or tissue graft and said T cell depleted immature hematopoietic cells are obtained from the same donor; and/or
(iv) comprises a co-transplantation of several organs.

11. The method of claim 1, wherein said non-myeloablative conditioning consists of said chemotherapeutic agent.

12. A method of reducing graft rejection and/or graft versus host disease (GVHD) or inducing donor specific tolerance in a subject in need thereof, the method comprising:
(a) conditioning a subject under non-myeloablative conditioning, wherein said non-myeloablative conditioning comprises a chemotherapeutic agent;
(b) transplanting into the subject a dose of T cell depleted immature hematopoietic cells obtained from a non-syngeneic donor, wherein said dose of said T cell depleted immature hematopoietic cells comprises less than $5\times10^5$ CD3+ cells per kilogram body weight of the subject, and wherein said dose comprises at least $5\times10^6$-CD34+ cells per kilogram body weight of the subject; and subsequently
(c) administering to the subject a therapeutically effective amount of cyclophosphamide, wherein said therapeutically effective amount comprises 25-200 mg cyclophosphamide per kilogram body weight of the subject, and wherein said cyclophosphamide is administered to the subject in two doses on days 3 and 4 following step (b), and wherein said subject is not treated with GVHD prophylaxis for more than 10 days post-transplant, thereby reducing graft rejection and/or GVHD.

13. The method of claim 12, wherein said conditioning further comprises conditioning the subject with in-vivo T cell debulking.

14. The method of claim 13, wherein said in-vivo T cell debulking is effected by antibodies, and optionally wherein said said antibodies comprise at least one of an anti-thymocyte globulin (ATG) antibody, an anti-CD52 antibody, and anti-CD3 antibody.

15. The method of claim 12, wherein said non-myeloablative conditioning further comprises a total body irradiation (TBI) or a total lymphoid irradiation (TLI).

16. The method of claim 12, wherein said conditioning is effected 1-10 days prior to said transplanting.

17. The method of claim 12, wherein said chemotherapeutic agent comprises at least one of Fludarabine, Busulfan, Melphalan, Thiotepa and cyclophosphamide.

18. The method of claim 12, wherein said dose of said T cell depleted immature hematopoietic cells:
(i) comprises $5\text{-}40\times10^6$ CD34+ cells per kilogram body weight of the subject; and/or
(ii) comprises less than $0.5\times10^6$ CD8$^+$ TCR$\alpha/\beta^-$ cells per kilogram body weight of the subject; and/or
(iii) comprises T cell depleted G-CSF mobilized peripheral blood progenitor cells; and/or
(iv) are obtained by T cell debulking; and/or
(v) are treated by B cell debulking.

19. The method of claim 12, wherein said amount of said cyclophosphamide is about 100-200 mg per kg body weight.

20. The method of claim 12, wherein each of said two doses of said cyclophosphamide comprises an amount of about 50 mg per kg body weight.

21. The method of claim 12, wherein the subject:
(I) is a human subject; and/or
(II) has a malignant disease and optionally wherein said malignant disease is a hematopoietic cancer; or
(III) has a non-malignant disease and optionally wherein said non-malignant disease is a genetic disease or disorder, a hematopoietic abnormality, an autoimmune disease or a metabolic disorder; or
(IV) is in need of a cell or tissue graft, and optionally:
(i) wherein cell or tissue graft is selected from the group consisting of a liver, a pancreas, a spleen, a kidney, a heart, a lung, a skin, an intestine and a lymphoid tissue or organ; and/or
(ii) wherein said cell or tissue graft is transplanted into the subject prior to, concomitantly with or following said transplanting said dose of said T cell depleted immature hematopoietic cells into said subject; and/or
(iii) wherein said cell or tissue graft and said T cell depleted immature hematopoietic cells are obtained from the same donor; and/or
(iv) comprises a co-transplantation of several organs.

22. The method of claim 12, wherein said non-myeloablative conditioning consists of said chemotherapeutic agent.

* * * * *